(12) United States Patent
Paydarfar et al.

(10) Patent No.: US 10,258,531 B2
(45) Date of Patent: Apr. 16, 2019

(54) SYSTEMS AND METHODS FOR INHIBITING APNEIC EVENTS

(75) Inventors: David Paydarfar, Newton, MA (US);
Riccardo Barbieri, Boston, MA (US);
Premananda Pai Indic, Northborough, MA (US); Ruby Kandah, Boston, MA (US); James Brian Niemi, Concord, MA (US); John Paul Osborne, Winchester, MA (US); Hani M. Sallum, Somerville, MA (US); Amanda V. Wozniak, Somerville, MA (US)

(73) Assignees: PRESIDENT AND FELLOWS OF HARVARD COLLEGE, Cambridge, MA (US); THE GENERAL HOSPITAL CORPORATION, Boston, MA (US); UNIVERSITY OF MASSACHUSETTS, Boston, MA (US)

( * ) Notice: Subject to any disclaimer, the term of this patent is extended or adjusted under 35 U.S.C. 154(b) by 895 days.

(21) Appl. No.: 14/342,050

(22) PCT Filed: Aug. 30, 2012

(86) PCT No.: PCT/US2012/053192
§ 371 (c)(1),
(2), (4) Date: Jun. 13, 2014

(87) PCT Pub. No.: WO2013/033433
PCT Pub. Date: Mar. 7, 2013

(65) Prior Publication Data
US 2014/0303458 A1 Oct. 9, 2014

Related U.S. Application Data

(60) Provisional application No. 61/528,994, filed on Aug. 30, 2011.

(51) Int. Cl.
*A61H 1/00* (2006.01)
*G06F 19/00* (2018.01)
(Continued)

(52) U.S. Cl.
CPC ............... *A61H 1/005* (2013.01); *A61B 5/01* (2013.01); *A61B 5/02055* (2013.01); *A61B 5/03* (2013.01);
(Continued)

(58) Field of Classification Search
None
See application file for complete search history.

(56) References Cited

U.S. PATENT DOCUMENTS 5,555,891 A * 9/1996 Eisenfeld ............. A61B 5/0809
600/534
6,062,216 A * 5/2000 Corn ....................... A61B 5/113
128/204.23
(Continued)

FOREIGN PATENT DOCUMENTS

JP 2008000222 A 1/2008
WO 96/28093 A1 9/1996

OTHER PUBLICATIONS

Bloch-Salisbury et al, Stabilizing immature breathing patterns of preterm infants using stochastic mechanosensory stimulation, J Appl Physiol (1985). Oct. 2009; 107(4): 1017-1027.*
(Continued)

*Primary Examiner* — Carl H Layno
*Assistant Examiner* — Qingjun Kong
(74) *Attorney, Agent, or Firm* — Nixon Peabody LLP

(57) ABSTRACT

Systems and methods are disclosed to monitor physiological for the occurrence of life threatening events and to apply stimulation to prevent the occurrence of said life-threatening events. Systems and methods for applying the stimulation
(Continued)

are also disclosed. These systems include applying the stimulation through via a mattress having a passive section and an active section, a plurality of focal stimulators, and/or an array to apply the stimulation are also disclosed. These devices include a mattress with an active region and a passive region, a stimulating array do deliver targeted stimulation, and a plurality of stimulators to apply focused stimulation.

9 Claims, 18 Drawing Sheets

(51) Int. Cl.
*A61B 5/00* (2006.01)
*A61B 5/01* (2006.01)
*A61B 5/11* (2006.01)
*A61F 5/56* (2006.01)
*A61M 21/02* (2006.01)
*A61H 23/02* (2006.01)
*A61B 5/03* (2006.01)
*A61B 5/0205* (2006.01)
*A61B 5/0468* (2006.01)
*A61B 5/08* (2006.01)
*A61B 5/024* (2006.01)
*A61M 21/00* (2006.01)

(52) U.S. Cl.
CPC .......... *A61B 5/0468* (2013.01); *A61B 5/0816* (2013.01); *A61B 5/11* (2013.01); *A61B 5/4818* (2013.01); *A61B 5/4836* (2013.01); *A61B 5/6892* (2013.01); *A61B 5/7275* (2013.01); *A61F 5/56* (2013.01); *A61H 1/001* (2013.01); *A61H 23/0245* (2013.01); *A61M 21/02* (2013.01); *G06F 19/00* (2013.01); *A61B 5/024* (2013.01); *A61M 2021/0022* (2013.01)

(56) References Cited

U.S. PATENT DOCUMENTS

| | | | | |
|---|---|---|---|---|
| 2006/0087325 | A1* | 4/2006 | Ariav | A61B 5/02444 |
| | | | | 324/637 |
| 2006/0089559 | A1* | 4/2006 | Barbieri | A61B 5/02405 |
| | | | | 600/509 |
| 2008/0051669 | A1* | 2/2008 | Meyer | A61B 5/02405 |
| | | | | 600/484 |
| 2012/0172730 | A1* | 7/2012 | Delos | A61B 5/0205 |
| | | | | 600/484 |

OTHER PUBLICATIONS

Penzel et al, Dynamics of Heart Rate and Sleep Stages in Normals and Patients with Sleep Apnea, Neuropsychopharmacology (2003) 28, S48-S53.*
Bloch-Salisbury et al., "Stabilizing immature breathing patterns of preterm infants using stochastic mechanosensory stimulation", Journal of Applied Physiology, vol. 107, No. 4, pp. 1017-1027, 2009.
Frey et al., "Irregularities and power law distributions in the breathing pattern in preterm and term infants", Journal of Applied Physiology, vol. 85, No. 3, pp. 789-797, 1998.
Jarvis et al., "Apnea patients characterized by 0.02 Hz peak in the multitaper spectrogram of electrocardiogram signals", Computers in Cardiology, 27, pp. 769-772, 2000.

* cited by examiner

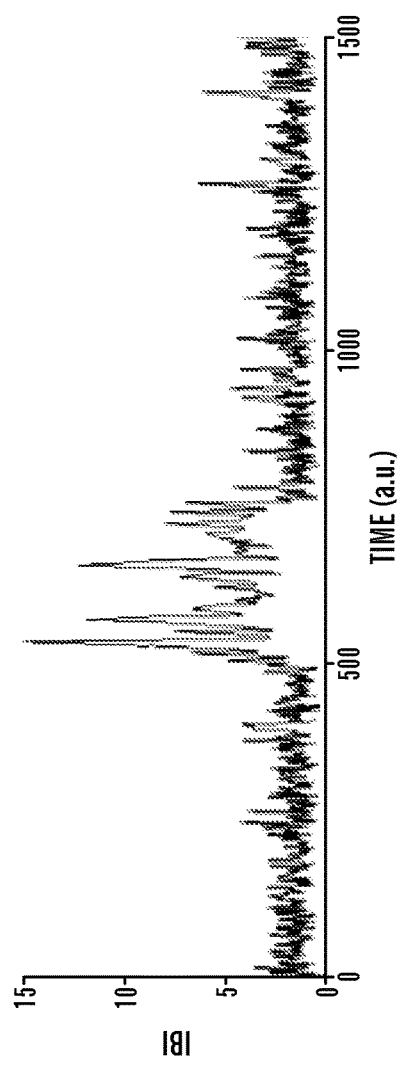
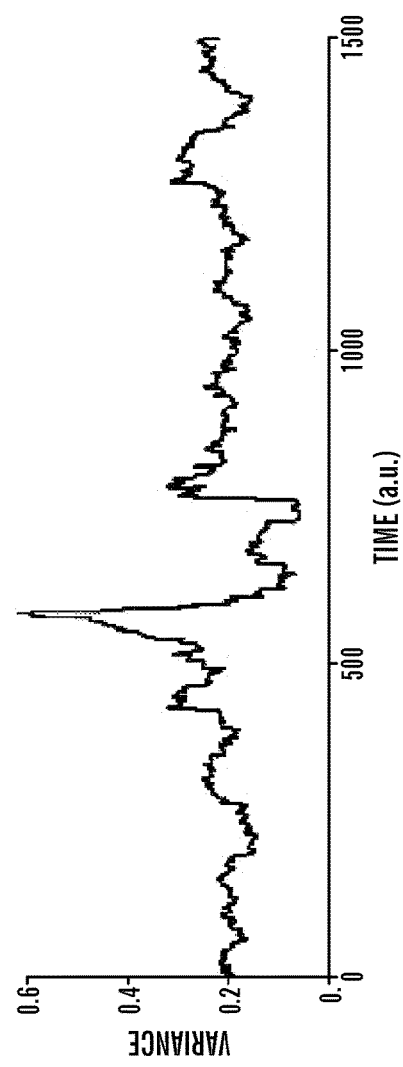
FIG. 1A
FIG. 1B

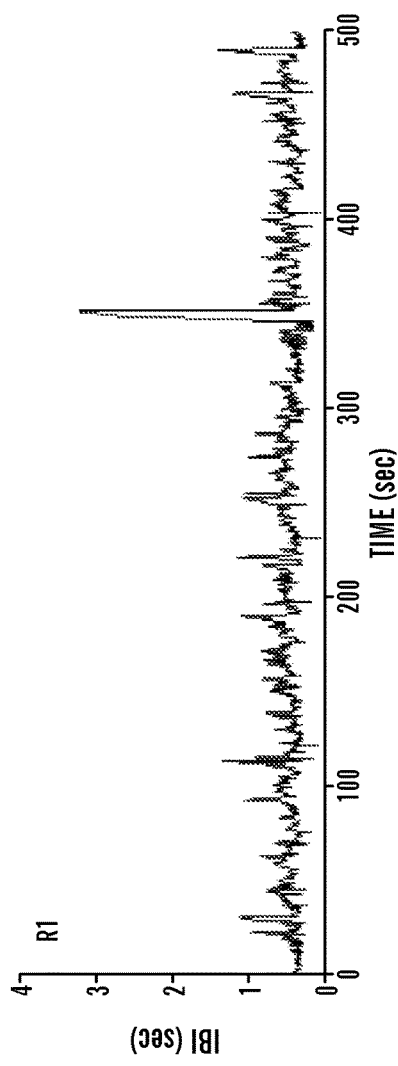
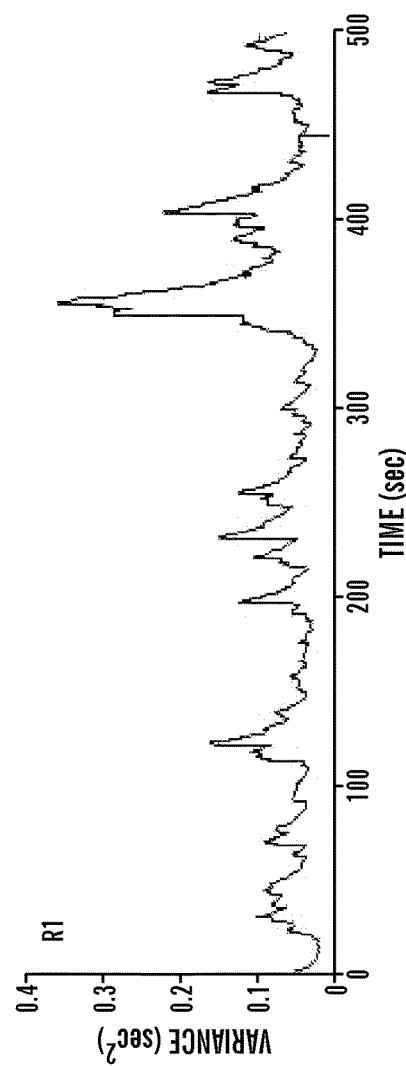
FIG. 3A
FIG. 3B

SYSTEMS AND METHODS FOR INHIBITING APNEIC EVENTS

CROSS-REFERENCE TO RELATED APPLICATIONS

This Application is a 35 U.S.C. § 371 National Phase Entry Application of International Application No. PCT/US2012/053192 filed Aug. 30, 2012, which designates the U.S., and which claims the benefit under 35 U.S.C. 119(e) of U.S. Provisional Application Ser. No. 61/528,994, filed Aug. 30, 2011, the contents of which are incorporated herein by reference in their entirety.

STATEMENT REGARDING FEDERALLY SPONSORED RESEARCH

This invention was made, in part, with government support under R01-HL084502, R01-HL49848, and/or R01-HL071884 awarded by the National Institutes of Health (NIH). The government has certain rights in the invention.

BACKGROUND

The present invention relates to methods and systems for inhibiting apneic events. More specifically, the present invention provides methods for monitoring physiological signals of a patient, predicting the occurrence of a life-threatening event such as apnea, and initiating a stimulus to lessen the severity of, or even prevent, the occurrence of the life-threatening event.

Infants with post-conceptional age of less than 36 weeks commonly have irregular breathing patterns with periodic and sporadic pauses in breathing, more commonly referred to as "apnea." One way to analyze breathing patterns is use the time interval between breaths, also referred to as the "interbreath interval."

Preterm infant breathing patterns are highly irregular, with rapid changes in measures of breathing. Standard statistical measures such as mean and variance of the interbreath interval have been used in an attempt to quantify the variability of breathing in preterm infants, but there is no known model available that can provide information in nonstationary breathing patterns using these statistical measurements.

It is believed that apneic events and poor respiratory function may also be contributing factors to Sudden Infant Death Syndrome. Even if not fatal, it is believed that apneic events and poor respiratory function may have a number of adverse consequences such as lengthening hospital stays, delaying development of an infant, or even irreparably harming the infant. These apneic events during infancy may affect the individual for their entire lifespan.

Therefore, it would be useful to describe pathological instabilities of breathing, track the dynamics in real time, and lessen the severity of an apneic event or entirely prevent an apneic event.

SUMMARY

According to one aspect of the present invention, a method for inhibiting an apneic events includes receiving physiological data from a subject, analyzing the received physiological data to detect an impending apneic event, and applying a stimulation to inhibit occurrence of the impending apneic event. The analyzing includes using a point-process model. The stimulation is applied after the occurrence of a predetermined event.

According to another aspect of the present invention, a system for inhibiting an apneic event includes an analysis module and a stimulating mechanism. The analysis module is configured to receive physiological data from a subject. The analysis module is also configured to analyze the received physiological data in real time using a point-process model to detect an impending apneic event. The stimulating mechanism is operatively coupled to the analysis module. The stimulating mechanism is configured to apply a stimulus to the subject. The applied stimulus inhibits the impending apneic event.

According to another aspect of the present invention, a system for inhibiting an apneic event includes an analysis module and a focal stimulating mechanism. The analysis module is configured to receive physiological data from a subject and to analyze the received physiological data in real time using a point-process model to detect an impending apneic event. The focal stimulating mechanism is operatively coupled to the analysis module. The focal stimulating mechanism is configured to apply a variable stimulus to one or more body parts of the subject. The applied stimulus then inhibits the impending apneic event.

According to yet another aspect of the present invention, a system for inhibiting an apneic event includes an analysis module and a stimulating array. The analysis module is configured to receive physiological data from a subject. The analysis module is further configured to analyze the received physiological data in real time using a point-process model to detect an impending apneic event. The stimulating array contains embedded actuators configured to be placed under the subject.

BRIEF DESCRIPTION OF THE FIGURES

FIG. 1A illustrates the interbreath interval of simulated data.

FIG. 1B is an instantaneous variance estimated by a point process model using the data of FIG. 1A.

FIG. 3A is an example from one continuous recording of a newborn rat.

FIG. 3B is a calculated variance of the data in FIG. 3A using the point process model.

DETAILED DESCRIPTION OF PREFERRED EMBODIMENTS

Figure 2:
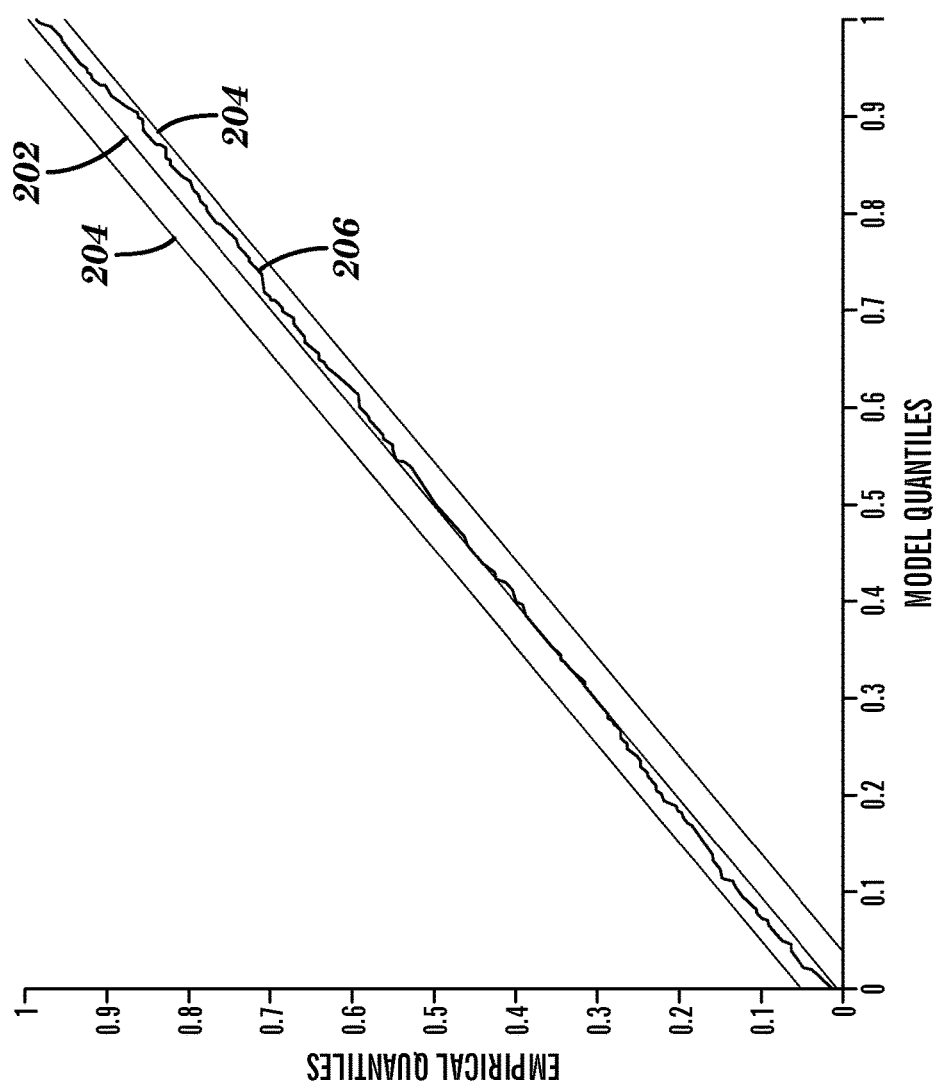
FIG. 2 shows a Kolmogorov-Smirnov plot of time-rescaled quantiles derived from the simulated data of FIG. 1A.

A point-process modeling framework may be used to develop algorithms for detecting and predicting life-threatening events in neonates. These life-threatening events include apnea, bradycardia, and hypoxia. A number of physiological signals may be monitored to automatically detect, and even predict the occurrence of life-threatening events. Detection or prediction of these events may decrease the severity of an event or even completely eliminate the event. Once detected, methods and systems may automatically apply a stimulus to a subject to decrease the severity of the event, revert the subject to the normal, rhythmic state, or even entirely prevent the occurrence of the event.

The application of stochastic resonance to non-linear physiologic systems may improve system performance. For example, the application of stochastic noise via mechanical vibration enhances the respiratory performance of infants with apnea. Additionally, it may be the case that stochastic resonance might also improve the pulmonary system's ability to optimize oxygen tension and gas exchange.

Modeling of Interbreath Intervals

Respiratory rhythm in mammals is governed by neural circuits within the brainstem that signal the timing and depth of each breath. Continuous ventilation results from recurrent bursts of inspiratory neuronal activity that controls the diaphragm via discrete phrenic motor neuron activations. One assumption that allows non-invasive measurement of neuronal inspiratory bursts is to assume that the peak of inspiration is a discrete event that marks the timing of neuronal inspiratory bursts. Another assumption that may be made is that interbreath interval dynamics are governed by continuous processes under the regulation of multiple feedback and feed-forward loops impinging upon the respiratory oscillator.

The interbreath interval of an infant follows a power-law distribution. The characterizing parameters of the power-law distribution are found to be sensitive to age (e.g., maturation). During a respiratory cycle, the end of inspiration and onset of expiration mark local maxima or local minima. For the purposes of this disclosure, the end of inspiration and onset of expiration will define local maxima unless otherwise noted. In an observation interval (0, T], the times where the local maxima occur may be defined as $0 < u_1 < u_2 < \ldots < u_k < \ldots < u_K \leq T$. Then, for any given respiratory event $u_k$, the waiting time until the next event obeys a history dependent log-normal probability density $f(t|H_k, \theta)$ as $$f(t|H_k, \theta) = \left[\frac{1}{2\pi\sigma^2(t-u_k)^2}\right]^{\frac{1}{2}} \exp\left\{-\frac{1}{2}\frac{(\ln(t-u_k) - \mu(H_k, \theta))^2}{\sigma^2}\right\} \quad (1)$$

Time t is any time greater than $u_k$. $H_k$ is the history of interbreath intervals up to $u_k$ represented as $H_k = \{u_k, w_k, w_{k-1}, \ldots, w_{k-p+1}\}$ where $w_k$ is the $k^{th}$ interbreath interval represented as $w_k = u_k - u_{k-1}$. Theta ($\theta$) is a vector of model parameters. The instantaneous mean is modeled as a p-order autoregressive process, $$\mu(H_k, \theta) = \theta_o + \sum_{j=1}^{p} \theta_j w_{k-j+1}.$$

The probability density in equation (1) defines the interbreath interval distribution with $\mu$ and $\sigma$ as the characterizing parameters. The local maximum-likelihood approach is employed to estimate $\theta$ and $\sigma$ at each instant of time t.

The local joint probability density of $u_{t-l}$: $u_t$ is used to calculate the local maximum likelihood estimate of $\theta$ and $\sigma$ where l is the length of the local likelihood observation interval. If a number $n_t$ of peaks in this interval are observed as $u_1 < u_2 < \ldots < u_{n_t} \leq t$ and if $\theta$ as well as $\sigma$ are time varying, then at time t, the maximum likelihood estimate of $\hat{\theta}_t$ and $\hat{\sigma}_t$ is to be the estimate of $\theta$ and $\sigma$ in the interval l. Considering the right censoring, the local log likelihood is obtained as $$\log f(u_{t-l:t} | \theta_t) = \sum_{i=2}^{n_t} w(t-u_i) \log f(u_i - u_{i-1} | H_{u_{i-1}}, \theta_t) + w(t-u_{n_t}) \log \int_{t-u_{x_t}}^{\infty} f(\theta | H_{u_{n_t}}, \theta_t) d\theta \quad (2)$$

where w(t) is a weighting function to account for faster updates to local likelihood estimation. The weighing function is $w(t) = \exp(-\alpha(t-u))$ where $\alpha$ is the weighting time constant that assigns the influence of a previous observation on the local likelihood at time t. The instantaneous estimate of the mean $\mu$ may be obtained using the autoregressive representation because $\theta$ can be estimated in continuous time. Similarly, the local likelihood estimate provides the instantaneous estimate of variance $\sigma^2$.

The interbreath interval probability model along with the local maximum likelihood method provides an approach for estimating the instantaneous mean and instantaneous variance of the interbreath interval. These measures provide information about the changes in the characteristics of the distribution and information related to the irregularity of breathing. The time-rescaled interbreath interval was computed to obtain a goodness-of-fit measure. The time-rescaled interbreath interval is defined as:

$$\tau_k = \int_{u_{k-t}}^{u_k} \lambda(t|H_t, \hat{\theta}_t) dt \qquad (3)$$

where $u_k$ represents the breathing events observed in (0, T) and $\lambda(t|H_t, \hat{\theta}_t)$ is the conditional intensity function defined as:

$$\lambda(t|H_t, \hat{\theta}_t) = f(t|H_t, \hat{\theta}_t, \hat{\sigma}_t) \left[ 1 - \int_{u_{n_t}}^{t} f(\theta|H_\theta, \hat{\theta}_\theta, \hat{\sigma}_\theta) d\theta \right]^{-1} \qquad (4)$$

The conditional intensity is the history dependent rate function for a point process that generalizes the rate function for a Poisson process. The $\tau_k$ values are independent, exponential, random variables with a unit rate. With a transformation $z_k = 1 - \exp(-\tau_k)$, the $z_k$ values become independent, uniform random variables on the interval (0,1]. A Kolmogorov-Smirnov test was used to assess the agreement between the transformed $z_k$ values and a uniform probability density. A Kolmogorov-Smirnov plot indicates agreement of the point-process model with the interbreath interval data series by plotting the transformed $z_k$ values versus the uniform density. A line close to the 45 degree diagonal from this plot indicates close agreement.

The Kolmogorov-Smirnov distance measures the largest distance between the cumulative distribution function of the transformed interbreath interval and the cumulative distribution function of a uniform distribution, both on the interval (0,1]. A shorter Kolmogorov-Smirnov distance indicates a better model in terms of goodness-of-fit.

Data were analyzed from both human and animals trials. Neonatal rats exhibit respiratory patterns and chemo-responses analogous to preterm infants. This includes both periodically occurring apnea episodes and sporadic apneas with bradycardia and hypoxemia. One- to two-day-old rats were placed in a sealed chamber and breathed through a face mask and pneumotachogram. Respiratory airflow was recorded through the mask. Pressure within the plethysmographically sealed chamber was measured and these measurements were used as an index of respiratory effort.

The tested preterm infant data included infants having a gestational age of less than 36 weeks and post-conceptional age greater than 30 weeks at the time of study. The infants were spontaneously breathing room air or receiving supplemental oxygen through nasal cannulae at a fixed flow rate. Respiratory inductance plethysmography of abdominal movements during spontaneous breathing (Somnostar PT; Viasys Healthcare, Yorbalinda, Calif.) was used to collect respiratory signal data at a sampling rate of 100 Hz.

The model was first tested using simulated data sets. Interbreath interval data series were simulated from a log-normal distribution with set mean $\mu$ and variance $\sigma^2$ values. FIG. 1A illustrates one of the simulated data series. The interbreath interval (IBI) of the simulated data is plotted over time, which is shown with arbitrary units. The simulated data kept the interbreath intervals relatively stable between times of zero and 500 units. Then, the interbreath intervals experienced significant variance between times of 500 to 800 units. After the time of 800 units, the simulated interbreath intervals returned to same levels as between times of zero and 500 units. These data were generated by keeping the interbreath interval variance $\sigma^2$ at a fixed value for times zero to 500, then randomly altering the variance $\sigma^2$ for times 500 to 800, and then returning to the initial variance $\sigma^2$ for times greater than 800. The mean value $\mu$ was kept at a constant level. That is, times zero to 500 and times greater than 800 simulated non-apneic sleep and times 500 to 800 simulated the occurrence of apneic events.

Referring to FIG. 1B, the instantaneous variance estimated by the developed point process model of order p=4, with local likelihood window i=100 and weighting time constant $\alpha$=0.01 along with a time resolution s=0.01 is shown for the data of FIG. 1A. As shown in FIG. 1B, the variance remained relatively constant at about 0.2 from times zero to 500, then sharply increased to about 0.6 and sharply fell to about 0.1 for times 500 to 800 before returning to about 0.2 for times after 800. This accurately estimated the mean $\mu$ and variance $\sigma^2$ for selected fixed mean $\mu$ and variance $\sigma^2$ values.

The goodness-of-fit of the point process model was analyzed. FIG. 2 shows a Kolmogorov-Smirnov plot of time-rescaled quantiles derived for the simulated data of FIG. 1A. The 95% confidence intervals 202 and theoretical values 204 were plotted along with the time-rescaled quantiles 206. A model is considered perfect if the quantiles 206 perfectly overlie the theoretical values 204. As shown, the time-rescaled quantiles 206 closely followed the line of theoretical values 204 and remain within the 95% confidence intervals 202.

Referring to FIG. 3A, an example from one continuous recording of a newborn rat R1 is shown. FIG. 3A plots the interbreath interval (IBI) over time. As shown, the interbreath interval remained relatively stable and exceeded 1 second at relatively few points. In newborn rats, an interbreath interval greater than 1 second indicates apnea. Some peaks that exceed 1 second occurred at times of, for example, about 25 seconds, about 105 seconds, about 225 seconds, about 350 seconds, and about 490 seconds. As the apnea occurs, the variance increases.

The variance in the interbreath interval is an indicator of stability of breathing. FIG. 3B shows the calculated variance of the newborn rat R1 data in FIG. 3A using the point process algorithm. As shown, the variance remained relatively stable, with significant peaks formed at, for example, about 25 seconds, about 105 seconds, about 200, about 225 seconds, about 350 seconds, about 400 seconds, and about 490 seconds. These peaks correspond with the apneic interbreath interval peaks in FIG. 3A.

Figure 4C:
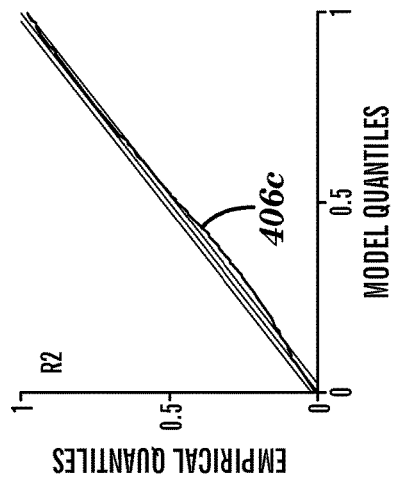
FIG. 4C shows a Kolmogorov-Smirnov plot of time-rescaled quantiles derived for data of a second newborn rat.
Figure 4D:
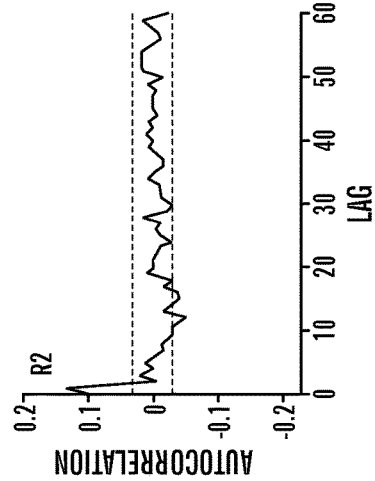
FIG. 4D shows an autocorrelation plot for the second newborn rat data of FIG. 4C.
Figure 4A:
FIG. 4A shows a Kolmogorov-Smirnov plot of time-rescaled quantiles derived for data of a newborn rat.
Figure 4B:
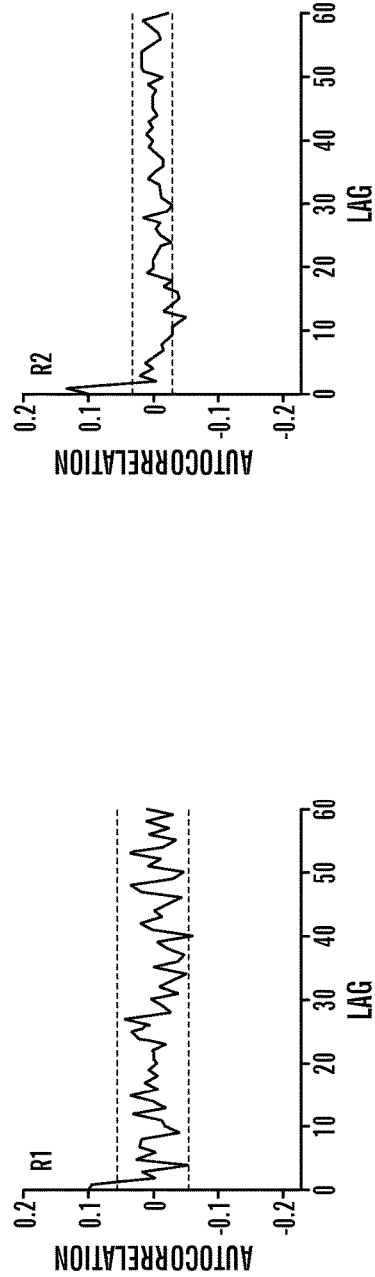
FIG. 4B shows an autocorrelation plot for the newborn rat data of FIG. 4A.

Referring to FIGS. 4A-4D, Kolmogorov-Smirnov plots of time-rescaled quantiles derived for data of two newborn rats R1, R2 was plotted along with the associated autocorrelation function for each. The theoretical values 402, 95% confidence intervals 404, and time-rescaled quantiles 406a,c for each newborn rat R1, R2 are shown in FIGS. 4A and 4C. The first newborn rat R1 was the same data used in FIGS. 3A and 3B. FIG. 4A shows the time-rescaled quantile 406a for the first newborn rat R1 closely following the theoretical values 402 along the 45 degree line, but approaching the upper 95% confidence interval 404 for model values between about 0.6 and about 0.8. FIG. 4B shows the autocorrelation of the first newborn rat R1 to remain within the corresponding confidence interval of (about ±0.05). FIG. 4C shows the time-rescaled quantile 406c for the second newborn rat R2 following the theoretical values 402 along the 45 degree line with a slight excursion beyond the lower 95% confidence interval 404 for model values between about 0.2 and about 0.4. FIG. 4D shows the autocorrelation of the second newborn rat R2 to remain within the corresponding confidence interval (about ±0.02).

Figure 5A:
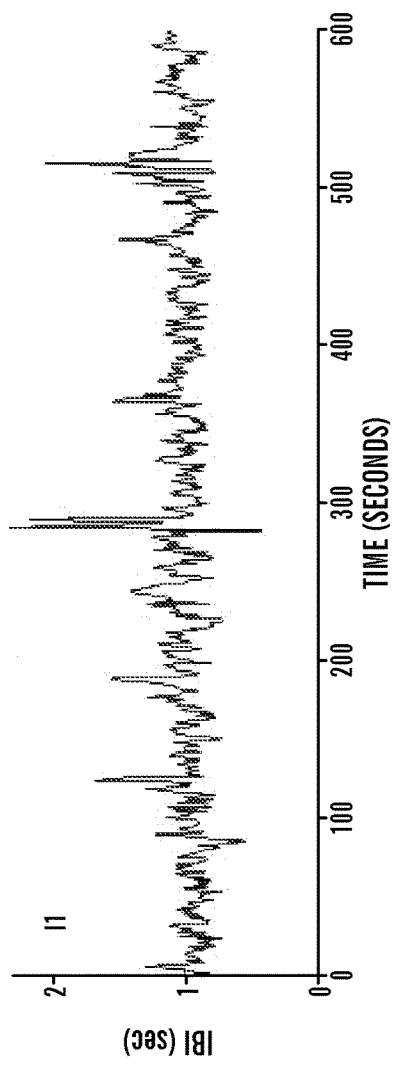
FIG. 5A shows one continuous recording of a human infant interbreath interval.

Referring to FIG. 5A, an example from one continuous recording of a human infant I1 is shown. The infant's I1 interbreath interval (IBI) remained at about one second peaks exceeding about 1.5 seconds at times of about 125 seconds, about 290, about 300 seconds, and about 510 seconds. In infants, the normal interbreath interval is about 1 second. Irregularity in breathing results in the interbreath interval varying from about 1 second to about 20 seconds. The change in interbreath interval is reflected as the variance.

Figure 5B:
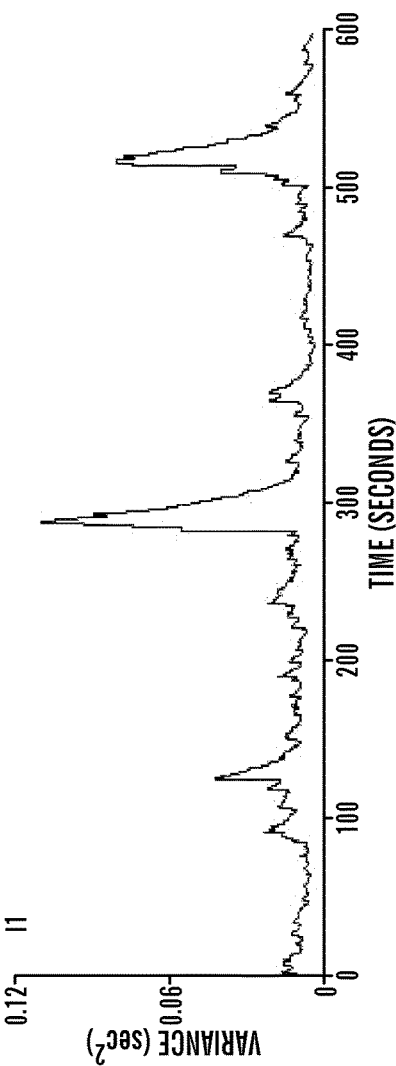
FIG. 5B shows the calculated variance of the data in FIG. 5A using the point process algorithm.

FIG. 5B shows the variance of the interbreath interval data (FIG. 5A) of the infant I1. The instantaneous variance increased during the apnea, suggesting larger variability. The variance remained relatively steady at approximately 0.01 sec$^2$. Significant peaks were seen at times of about 125 seconds, about 290 to 300 seconds, and about 510 seconds.

Figure 6B:
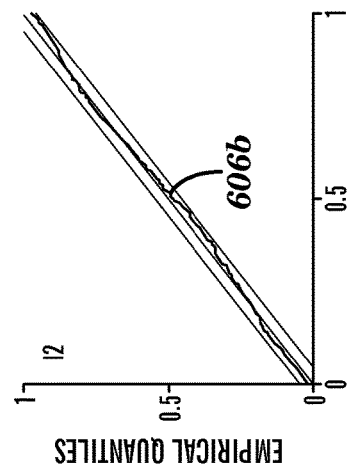
FIG. 6B shows the Kolmogorov-Smirnov plot of a second infant data.
Figure 6D:
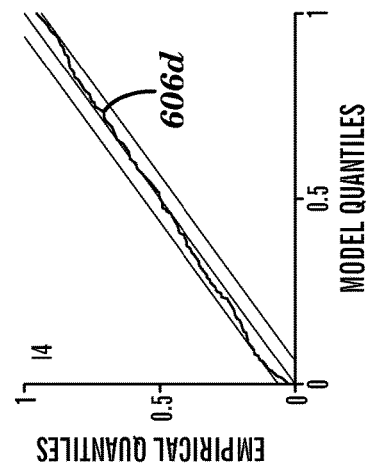
FIG. 6D shows the Kolmogorov-Smirnov plot of a fourth infant data.
Figure 6A:
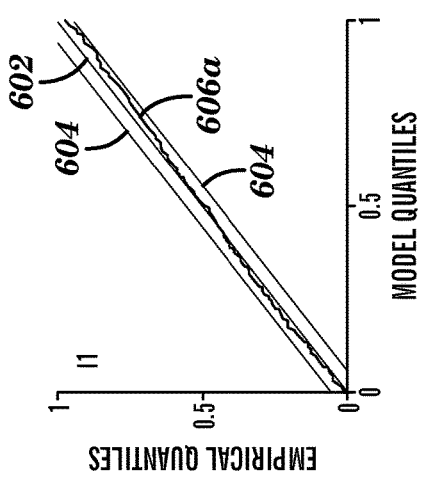
FIG. 6A shows the Kolmogorov-Smirnov plot of the infant data of FIG. 5A.

FIGS. 6A-6D provide the Kolmogorov-Smirnov plots from four infants I1-I4, respectively. FIG. 6A shows the Kolmogorov-Smirnov plot of the first infant I1 data from FIGS. 5A and 5B. The time-rescaled quantiles 606a for the first infant I1 closely track the theoretical values 602 along the 45 degree line, but approached the lower 95% confidence interval 604 for model quantiles of about 0.8 to about 1.0.

FIG. 6B shows the Kolmogorov-Smirnov plot of a second infant I2 data. The time-rescaled quantiles 606b for the second infant I2 closely tracked the theoretical values 602 along the 45 degree line, but approached the lower 95% confidence interval 604 for model quantiles of about 0.9 to about 1.0.

Figure 6C:
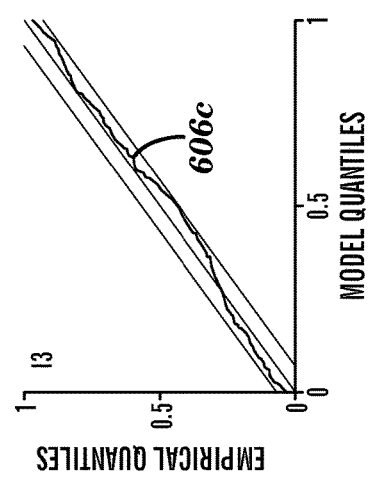
FIG. 6C shows the Kolmogorov-Smirnov plot of a third infant data.

FIG. 6C shows the Kolmogorov-Smirnov plot of a third infant I3 data. The time-rescaled quantiles 606c for the third infant I3 tracked the theoretical values 602 along the 45 degree line. The time-rescaled quantiles 606c approached the upper 95% confidence interval 604 for model quantiles of about 0 to about 0.2 and approached the lower 95% confidence interval 604 for model quantiles of about 0.4 to about 0.6 and about 0.9 to about 1.0.

FIG. 6D shows the Kolmogorov-Smirnov plot of a fourth infant I4 data. The time-rescaled quantiles 606d for the fourth infant I4 closely tracked the theoretical values 602 along the 45 degree line. The time-rescaled quantiles 606d approached the upper 95% confidence interval 604 for model quantiles of about 0.1 to about 0.2 and approached lower 95% confidence interval 604 for model quantiles of about 0.9 to about 1.0.

The time varying evolution of the characterizing parameters were estimated to represent the dynamic nature of breathing and thereby provide a time-varying measure of irregularity in breathing according to Equation 1 above.

The instantaneous mean is modeled as a p-order autoregressive process as $$\mu(H_k, \theta) = \theta_o + \sum_{j=1}^{p} \theta_j w_{k-j+1} \qquad (5)$$

The probability density in Equation 1 defines the interbreath interval distribution with mean μ and variance σ as the characterizing parameters. At each instant of time t, a local maximum-likelihood approach was used to estimate μ and σ. To calculate the local maximum likelihood estimate of μ and σ, the local joint probability density of $u_{t-l}:u_t$ is defined as the length of the local likelihood observation interval. The maximum likelihood estimate of $\hat{\theta}_t$ and $\hat{\sigma}_t$ is approximated as the estimate of θ and σ in the interval l at time t if $n_t$ peaks are observed within this interval as $u_1 < u_2 < \ldots < u_{n_t} \leq t$ and if θ as well as σ are time varying. Thus, for a p-order of 4, Equation 1 becomes:

$$f(t | H_k, \theta) = \left[\frac{1}{2\pi\sigma^2 w_k}\right]^{\frac{n-2}{2}} \exp\left\{-\frac{1}{2}\frac{(\ln(w_k) - \mu(H_k, \theta))^2}{\sigma^2}\right\} \qquad (6)$$

The order, p, can be set to a different level based on a particular application.

Given Eq (6), the local log-likelihood for an observation window $n_t$ can be defined as:

$$\log f(u_{t-l:t} | \theta_t) = \sum_{i=2}^{n_t} w(t - u_i) \log f(u_i - u_{i-1} | H_{u_{i-1}}, \theta_t) + \\ w(t - u_{n_t}) \log \int_{t-u_{n_t}}^{\infty} f(\partial | H_{u_{n_t}}, \theta_t) d\partial \qquad (7)$$

where w(t) is a weighting function to account for faster updates to local likelihood estimation. The weighing function was expressed as w(t)=exp(-α(t-u)) where α is the weighting time constant that assigns the influence of a previous observation on the local likelihood at time t. The instantaneous estimate of the mean μ is obtained using the autoregressive representation because θ can be estimated in continuous time. Similarly the local likelihood estimate provides the instantaneous estimate of variance σ$^2$ as $$\sigma^2 = (\ln(w_k) - \mu_k)^2 / n_t \qquad (8)$$

Thus the instantaneous mean in Equation 5, along with the variance in Equation 8 determines the characterizing parameters of the algorithm that track the instability of breathing in real time.

Modeling of Heartbeat Intervals

Additionally or alternatively, other physiological signals can be monitored to detect or predict the occurrence of a life-threatening event. A point-process model was developed using electrocardiograph and respiratory signals as primary signals. All other physiological signals were used as covariates in the predictive algorithm.

The peak of the electrocardiogram, also known as the R-wave event, is treated as a point process. The distribution of the interbeat intervals is used for developing the probabilistic modeling framework for the algorithm. An interbeat interval is the time elapsed between two successive R-wave peaks and is also known as an R-R interval.

A probabilistic model of a dynamical system observed through a point process can be used to meaningfully analyze heartbeat data. The heartbeat intervals are the times between R-wave events. These R-wave events correspond to the electrical impulses from the heart's conduction system, which initiate ventricular contractions. Therefore, the R-wave events form a point process because the events are a sequence of discrete occurrences in continuous time. Additionally, the autonomic nervous system is the principal dynamic system that modulates the dynamics of the heartbeat intervals. Thus, premature infant heartbeats can be accurately characterized by point process models of the R-R intervals.

The point process framework can be related to other variables, including respiratory activity, movement, pulse and other related physiological variables. These relations may be used to establish new measures of control dynamics by the autonomic nervous system. A new statistical framework was developed using the indices obtained from the model. This combined framework combined measures sleep state, respiratory dynamics, and cardiovascular control for predicting life-threatening events in infants.

For any R-wave event $u_k$, the waiting time until the next R-wave event obeys a history-dependent inverse-Gaussian probability density. This is expressed as $f(t|H_{u_k}, \theta)$, where $t$ is any time greater than $u_k$, $H_{u_k}$ is the history of R-R intervals up to $u_k$, and $\theta$ is a vector of model parameters. The waiting time until the next R-wave event is also the length of the next R-R interval. The model is defined as:

$$f(r|H_{u_k}, \theta) = \tag{9}$$

$$\left|\frac{dt}{dr}\right| f(t|H_{u_k}, \theta) = \left[\frac{\theta^*_{p+1}}{2\pi r}\right]^{\frac{1}{2}} \exp\left\{-\frac{1}{2}\frac{\theta^*_{p+1}[1-\mu^*(H_{u_k}, \theta)r]^2}{\mu^*(H_{u_k}, \theta)^2 r}\right\}$$

where $\mu^*(H_{u_k}, \theta) = c^{-1}\mu(H_{u_k}, \theta)$ and $\theta_{p+1}^* = c^{-1}\theta_{p+1}$. The mean and standard deviation of the heart rate probability density, respectively, are:

$$\mu_{HR} = \mu^*(H_{u_k}, \theta)^{-1} + \theta^{*-1}_{p+1} \tag{10}$$

$$\sigma_{HR} = \left[\frac{2\mu^*(H_{u_k}, \theta) + \theta^*_{p+1}}{\mu^*(H_{u_k}, \theta) \cdot \theta^{*2}_{p+1}}\right]^{\frac{1}{2}} \tag{11}$$

The mean in Equation 9 becomes $$\mu(H_{u_k}, \theta, \rho, \gamma, \eta) = \theta_o + \sum_{j=1}^{p} \theta_j w_{k-j+1} + \sum_{j=1}^{q} \rho_j RESP_{k-j+1} + \tag{12}$$

$$\sum_{j=1}^{m} \gamma_j SaO2_{k-j+1} + \sum_{j=1}^{s} \eta_j MOV_{k-j+1} \ldots > 0$$

where RESP refers to the instantaneous lung volume measure, SaO2 refers to arterial-blood oxygen saturation, and MOV refers to movements monitored by electromyographic signals. The values of each are sampled in correspondence to the beat series because they are considered together with autoregressions on the R-R intervals. All other physiological signals act as covariates. Additionally, the amplitude of the respiration is included as one of the covariates because both the amplitude and the timing are important features to define the stability of breathing. It is contemplated that one or more of these covariates (e.g. the amplitude of the respiration) may be excluded from analysis.

Both the maximum local likelihood algorithm and the adaptive filtering algorithm were used to fit the model with covariates to the data. This allows for estimation of new indices of cardiovascular control defined as a function of the parameters $\theta = [\theta_0 \ldots \theta_p]$, $\rho = [\rho_1 \ldots \rho_q]$, $\gamma = [\gamma_1 \ldots \gamma_q]$, $\eta = [\eta_1 \ldots \eta_s]$.

The model for interbreath interval is the same as discussed above with the mean interbreath interval defined by considering other physiological signals as covariates. The dynamics of poles of the auto-regression as well as the instantaneous power can serve as indices of the cardio-respiratory dynamics because the instantaneous mean is represented as an autoregressive process in both the inter-breath interval model and the R-R interval model. The respiratory system was considered stable if the poles were inside the unit circle and unstable if the poles were outside of the unit circle. The degree of instability is defined using the number of poles outside the unit circle.

The resulting indices of cardio-respiratory dynamics are related to the life-threatening events including sleep state as a variable in the probability function. The model seeks to characterize the probability of onset of a life threatening event given the infant's physiological and autonomic state, as:

$$Pr(\text{Apnea}) = f(\text{Sleep}, H_{u_k}, \theta, \rho, \gamma, \eta) \tag{13}$$

This function was modeled using a framework including classifiers, regression analysis, principal component analysis, state vector machines, and adaptive filters, namely a Kalman filter. The function includes the indices defined for the R-R interval as well as interbreath interval. For the R-R interval model and interbreath interval models, a parametric approach was pursued. This approach characterized specific indices from the auto-regression models. The parameters were estimated using local likelihood and/or adaptive algorithms. The model fits were tested using well-established goodness-of-fit analysis. After determining the functions, indices extracted from this new explicit framework were used to statistically assess the predictive power of the model across the available database, both with and without vibrotactile stimulation.

The observations outlined above can be used to develop systems and devices that measure, indicate, and initiate other processes when a predetermined condition is met (e.g., a specified interbreath interval, R-R interval, and/or interbreath interval variability condition). The initiation of other processes can take many forms. One non-limiting example is to warn an individual when a predetermined condition is met or predetermined boundaries are crossed. The warning could include, for example, triggering an alarm, illuminating a light, initiating a sound, altering a display device such as a monitor, creating notes in medical records or chart recordings, sending a text alert such as an e-mail, SMS, or MMS message, and/or sending an automated phone call. Additionally or alternatively, a corrective therapy can be automatically applied upon the happening of a predetermined condition. One non-limiting example would be to initiate vibration of a neonatal mattress for avoiding sleep apnea. Moreover, a single device can perform multiple functions such as the example of a neonatal mattress with sensor, actuators, and computation incorporated measuring respiration of an infant and using algorithm and process described to initiate a therapy or action to stimulate and restore breathing.

The point process model was applied to an existing infant database in order to understand the respiratory dynamics related to mechanosensory stimulation. It was shown that the variance of the interbreath intervals is an important indicator of instability of breathing, with higher variance indicating irregular breathing and increased apnea and lower variance indicating the stable breathing patterns and decreased apnea.

It was expected that stimulation would induce rapid changes in interbreath interval variance because mechanoreceptor stimulation affects the respiratory oscillator via neural signals. Surprisingly, analysis of eleven infants revealed that the respiratory system exhibits relatively slow dynamics in interbreath interval variance in response to both initiation and removal of mechanoreceptor stimulation.

Figure 7A:
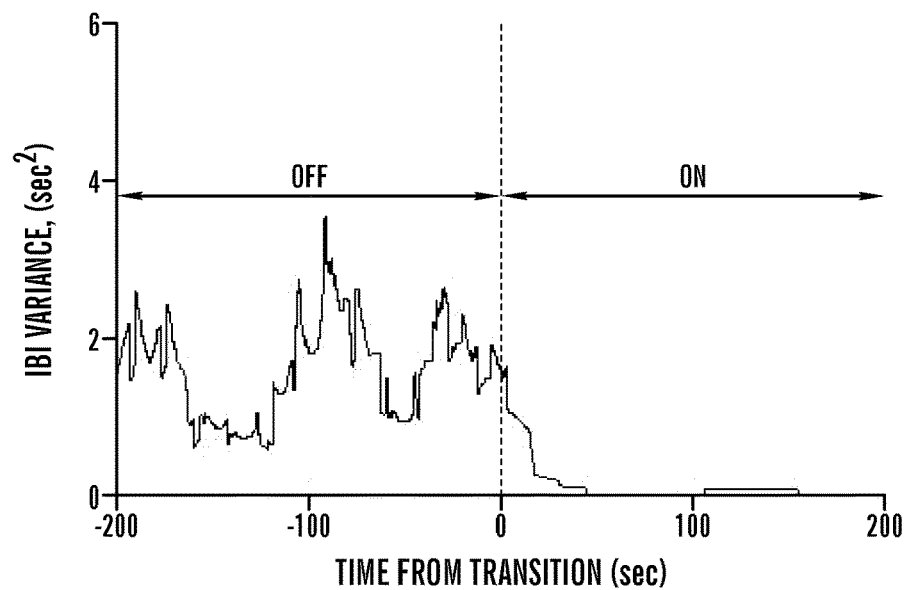
FIG. 7A shows an example of interbreath interval variance over time when stimulation was initiated.
Figure 7B:
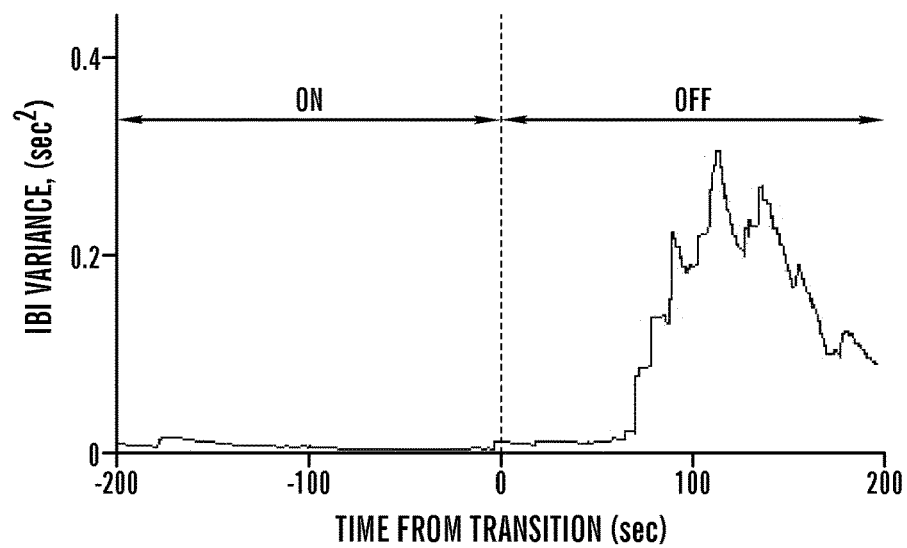
FIG. 7B shows an example of interbreath interval variance over time when stimulation was terminated.

Referring now to FIGS. 7A and 7B, an example of the change in interbreath interval variance in response mattress stimulation is shown. FIG. 7A shows interbreath interval variance over time when the mattress stimulation was initiated. During times −200 to 0, no stimulation was present and the interbreath interval showed considerable variance. Stimulation was initiated at time 0. Once stimulation was initiated, the variance began to decline until no variance was noticed at approximately 60 seconds. Between 60 and 200 seconds there is almost no variance present.

FIG. 7B shows interbreath interval variance over time when the mattress stimulation was removed. During times −200 to 0, stimulation was present and the interbreath interval showed almost no variance. Stimulation was terminated at time 0. Once stimulation was terminated, the level of variance remained at almost zero until a sharp increase at approximately 60 seconds. Between 60 and 200 seconds, variance began fluctuating again. The study of eleven infants showed that the interbreath interval variance evolved to the new level within approximately one minute.

The interbreath interval data in FIGS. 7A and 7B was obtained by implementing the point process model of respiration. This revealed a parameter that is necessary for a device to prevent apnea. As shown in FIGS. 7A and 7B, impending apnea must be anticipated within approximately one minute in order to actuate the mechanosensory stimulus in time to prevent the apnea. Similarly, removal of the stimulus could result in persistent beneficial after-effects that maintain stability of breathing for up to approximately one minute after cessation of the stimulus. It is contemplated that this lag time might be different depending on factors such as post-conceptional ages, gestational age, concurrent conditions that might affect signaling within the respiratory control system, monitoring method, etc. The respiratory response time to stimulation onset and offset can be estimated for data sets from individual infants, and the resultant time constant can be automated and incorporated into the algorithm used to control the actuators that provide feedback mechanosensory stimulation to the respiratory control system.

In accordance with one embodiment, the present invention can be used to track the instability of breathing in infants, and in particular, preterm infants. Preterm infants with post-conceptional age of less than 36 weeks commonly have irregular breathing patterns with periodic and sporadic pauses in breathing. Variance has been shown to be a good marker for the incidence of apnea and hypoxia events.

It is essential to correctly quantify the irregularity of the breathing patterns, so that appropriate magnitude as well as duration of mechanosensory (vibrotactile) stimulation can be provided to improve the breathing patterns in preterm infants.

Figure 8A:
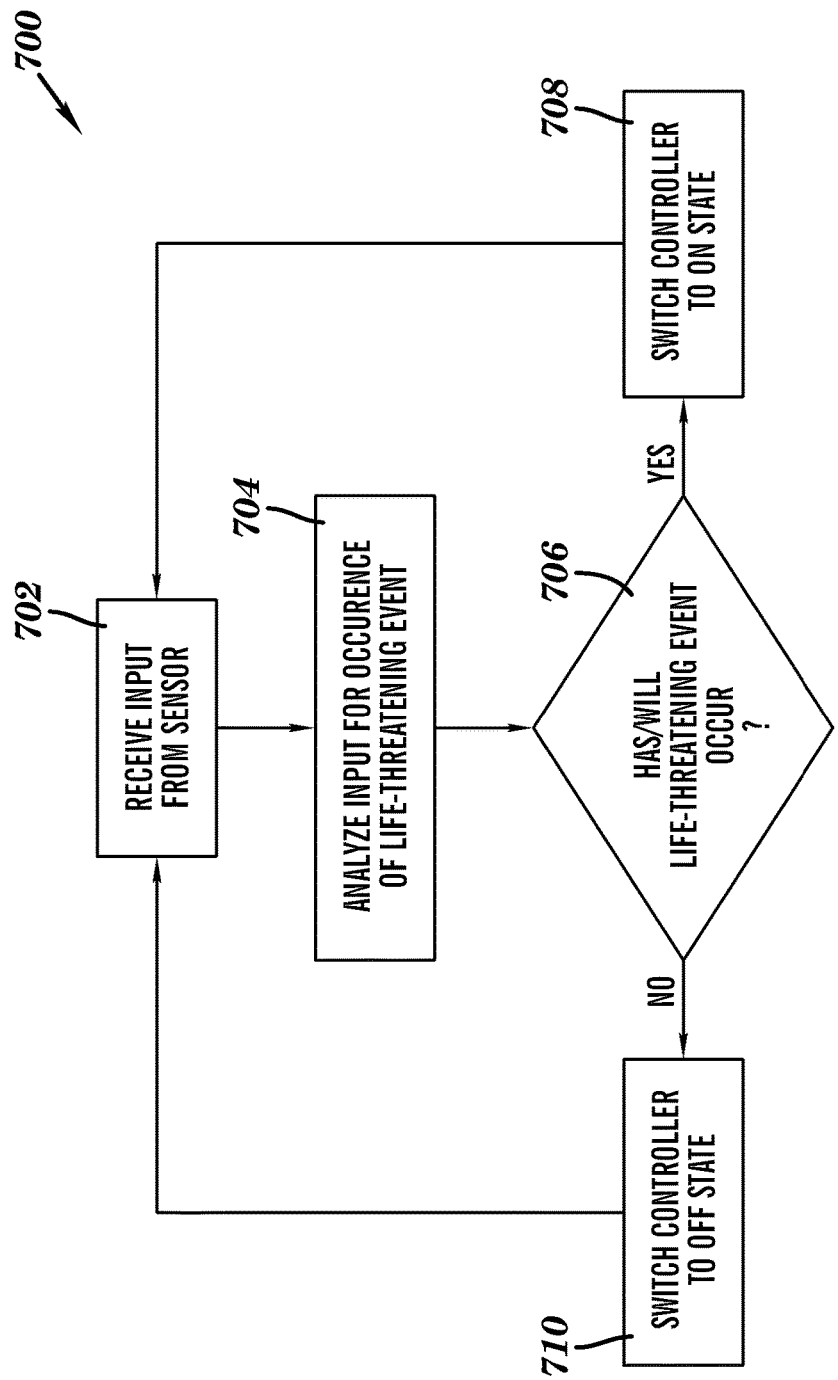
FIG. 8A shows a flowchart for an algorithm 700 to monitor physiological instabilities in real time.

In accordance with one embodiment of the invention, FIG. 8A shows a flowchart for an algorithm 700 to monitor physiological instabilities in real time. Characterizing parameters (e.g. variance, heartbeat) can be used to assess likelihood of a life-threatening event occurring based on the monitored physiological factors. Step 702 receives input from sensors. By way of non-limiting example, these sensors can monitor heartbeat and/or breathing patterns. Step 704 analyzes the input for the occurrence of a life-threatening event. The occurrence of the life-threatening event may either be occurring contemporaneously with the analysis and monitoring, or it may occur in the future. By way of non-limiting example, a threshold value can be set while monitoring instantaneous breathing variance. At decision box 706, it is determined whether a life-threatening event has or will occur. By way of non-limiting example, a threshold or set-point for variance indicates whether or not a life-threatening event has occurred. If the value is above a certain threshold, a life-threatening event has occurred.

If the algorithm detects that a life threatening event has or will occur, a controller is switched to the ON state at step 708. The controller is adapted to deliver vibrotactile stimulation to the source of monitored input (e.g. an infant). The algorithm 700 continues to receive input from the input sensor at step 702. It is contemplated that the controller may remain in the ON state for a predetermined amount of time, or until a precondition is met.

If the algorithm does not detect a life threatening event at decision box 706, the controller is biased to the OFF state at step 710. The algorithm 700 then continues to receive input from the sensor at step 702.

Figure 8B:
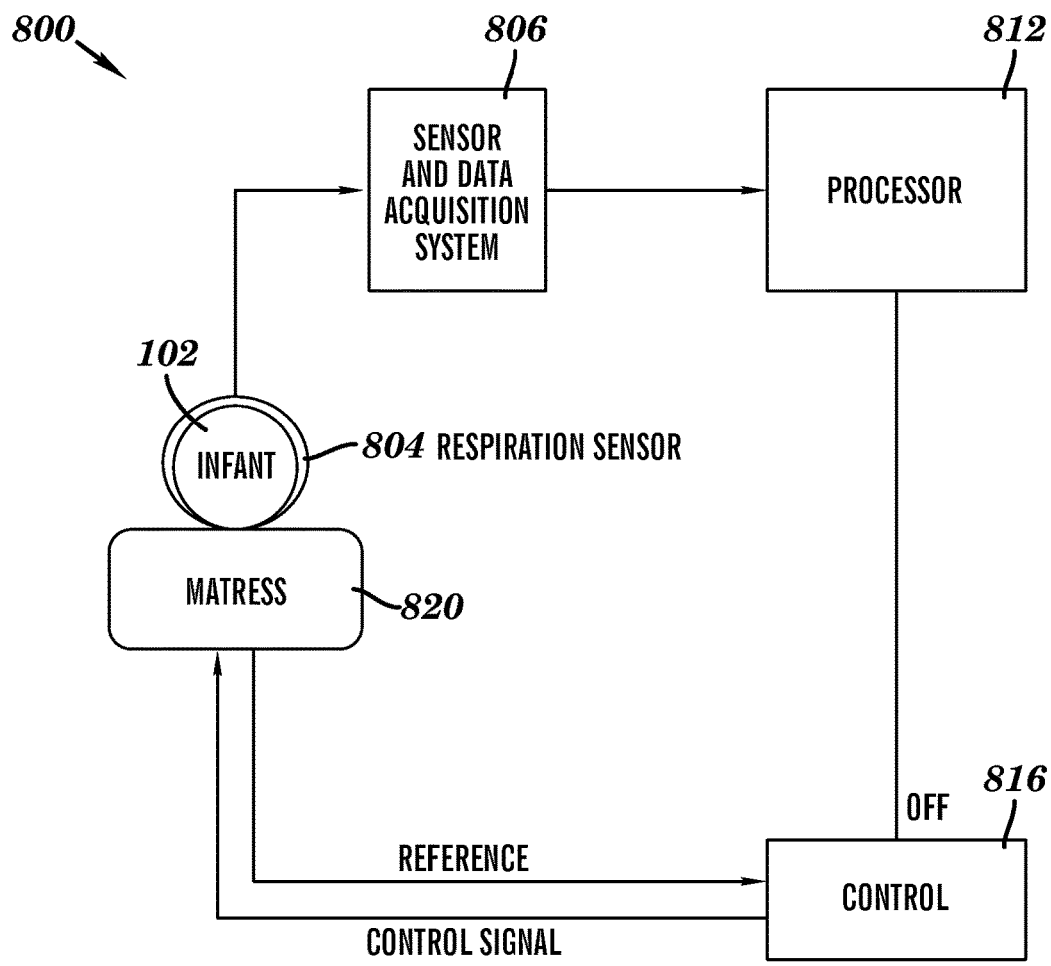
FIG. 8B shows a system to monitor instabilities in breathing over time and control stimulation according to one embodiment.

FIG. 8B shows a system 800 that monitors instabilities in breathing in real time according to one embodiment. The system 800 of FIG. 8B includes a respiration sensor 804, a sensor and data acquisition system 806, and a controller 810. The system 800 includes a vibrotactile stimulation mattress 820, which is connected to the controller 810. The respiration sensor 804 can be fastened to an infant 802 by, for example, a band or strap. The respiration sensor 804 measures the respiration of the infant 802. The sensor and data acquisition system 806 receives signals from the respiration sensor 804 and produces a respiration signal that is input to a respiration signal processor 812 of the controller 810. The respiration signal processor 812 uses the respiration signal to produce a variance value. The variance value can be compared to a threshold or set-point by a compare module (e.g., software module, hardware component, comparator, etc.) and used to turn ON or OFF a mattress controller 816. The mattress controller 816 is generally biased in the OFF status, until the variance meets or exceeds the threshold. When the mattress controller 816 is in the ON state, the mattress 820 produces one or more stimuli to restore breathing.

Isolation Mattress

Figure 9:
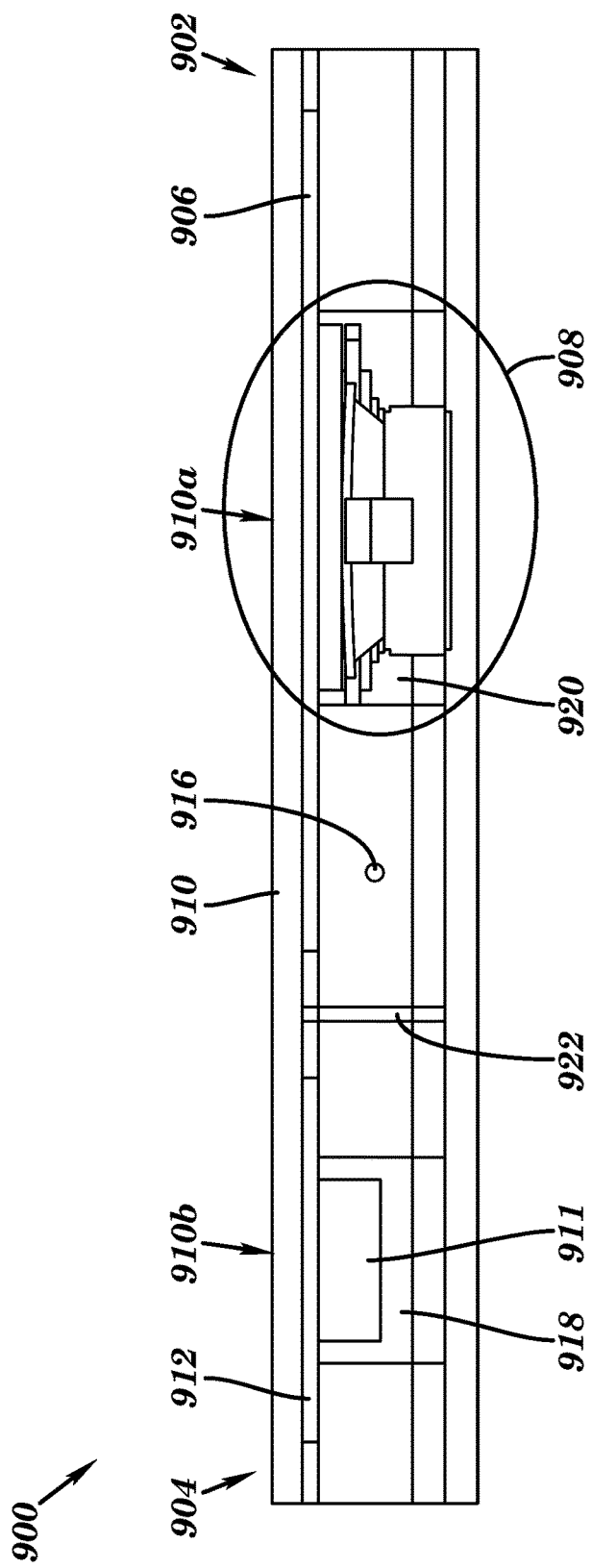
FIG. 9 depicts the cross-section of a therapeutic mattress design that applies isolated stochastic resonance mechano-stimulation to a portion of the mattress according to one embodiment.

FIG. 9 depicts an isolation mattress 900 that applies isolated stochastic resonance mechanostimulation to a specific portion of the mattress according to one embodiment. The isolation mattress 900 includes a body 916. The body 916 includes an active region 902, a passive region 904, a top surface 910a, 910b, and a plurality of voids 918, 920, 922. The active region 902 includes an actuator 908 attached to an active soundboard 906. The passive region 904 includes an inertial device 911 attached to a passive soundboard 912. A passive-section void 918 is located around the inertial device 911. An active-section void 920 is located around the actuator 908. A soundboard void 922 is located between the active and passive soundboards 906, 912.

The active region 902 interacts with parts of an infant's body that can receive stimulation with little or no adverse consequences. These body parts include the legs and torso of the infant. The active region 902 is generally rectangular and occupies top surface 910a area, which is about two-thirds of the isolation mattress 900. It is contemplated that other shapes and sizes may be used be used to obtain the above described benefits.

The active soundboard 906 and the actuator 908 impart vibrational stimulation on the top surface 910a in the active region 902. The actuator 908 is attached to the active soundboard 906 such that movement of the actuator 908 moves the active soundboard 906. The active soundboard 906 is disposed below the top surface 910a such that at least a portion of the vibrations are imparted on the top surface 910a. For example, the active soundboard 906 can be placed approximately one-half inch below the top surface 910a. It is contemplated that other distances may be employed to achieve desired physical and vibrational properties of the top surface 910. For example, the soundboard may be placed from 0.4 inches to 0.6 inches, from 0.25 inches to 0.75 inches, from 0.1 inches to 1.0 inch, or even greater than 1.0 inch from the top surface 910. Inches The passive region 904 interacts with parts of an infant's body that are more sensitive to stimulation, such as the head. The passive region 904 is shown as being generally rectangular and occupies top surface 910a area, which is about one-third of the total top surface area of the isolation mattress 900. It is contemplated that other shapes and sizes may be used be used to obtain the above described benefits. It is additionally contemplated that the size of the active region 902 relative to the passive region 904 may be altered.

The passive region 904 is mechanically isolated from the active region 902. The inertial device 911 is attached to the passive soundboard 912 such that the inertial device 911 helps to dampen vibrations from the active soundboard 906 and actuator 908. In the illustrated embodiment, the inertial device 911 is a passive inertial device a mass attached to the passive soundboard 912. This mass is 660 g of aluminum rigidly attached to the passive soundboard 912. It is contemplated that the masses may be made of different materials or weights. It is also contemplated that the inertial device 911 may be a device that actively cancels vibrations imparted on the passive soundboard 912.

The body 916 may comprise various materials. By way of non-limiting example, an open-cell foam, gel, or other viscoelastic material may be used to damp the vibrations from the active soundboard 906 and the actuator 908. Additionally, the voids 918, 920, 922 assist in inhibiting vibrations from passing to the passive section. The passive-section void 918 prevents or inhibits vibrations from being imparted to the inertial device 911. The active-section void 920 prevents or inhibits the actuator 908 from imparting vibrations on the body 916. The soundboard void 922 prevents or inhibits vibrations from directly passing between the active soundboard 906 and the passive soundboard 912. It is also contemplated that any or all of the plurality of voids may be replaced with visco-elastic damping materials that alter and/or modify the transmission of vibrations from the active soundboard 906 and actuator 908 to the passive region 904. By way of non-limiting example, Young's Modulus, density, and/or visco-elastic properties may be considered when selecting materials. Sufficiently dissimilar material may result in improved isolation characteristics because vibration transmission between materials is a function of the area of contact in addition to the impedance of the materials to a specific type of vibration.

Additionally, the isolation mattress 900 may indicate the active and the passive regions 902, 904 to an individual. Examples of this include using visual indicia on the top surface 910, the body 916, and/or on a cover placed over the isolation mattress 900. The cover may be made from, for example, polymeric materials including medical grade vinyl.

Figure 10:
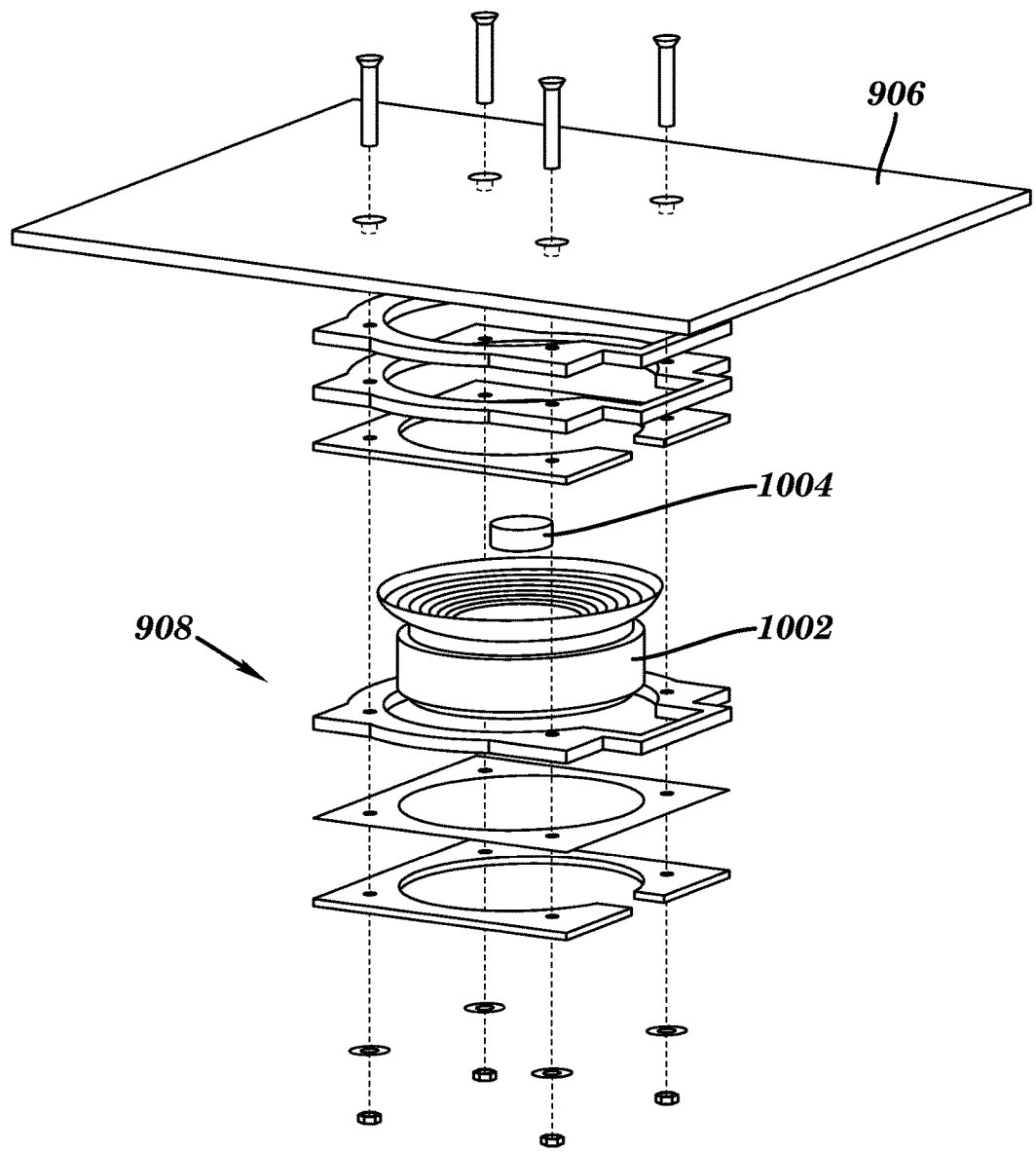
FIG. 10 shows an exploded view of an active assembly according to one embodiment.

Referring now to FIG. 10, an exploded view of the actuator 908 is shown with the active soundboard 906 according to one embodiment. In the illustrated embodiment, the movement of the actuator 908 is obtained by imparting a drive signal to an audio driver 1002. A mass 1004 was added to the audio driver 1002 to increase output.

The isolation mattress 900 was tested against a single-bodied mattress. Both mattresses were 23 inches long, 12 inches wide, and 3.25 inches tall. All soundboards were located one-half inch below the top surface of the mattress.

The specifications for the single-bodied mattress included: an active soundboard being plywood; an actuator being a "woofer" audio driver of unknown origin; a body being a low-density foam rubber material; and the surface covering being a vinyl material.

The specifications for the isolation mattress 900 used in testing included: the active and passive soundboards 906, 912 being acrylic plastic; the inertial device 911 being a 660 g aluminum mass; the actuator 908 being an MCM model 1170 "woofer" audio driver that was modified to remove the driver cone and shorten the overall height; a 38.6 g mass 304 stainless steel mass was added to the audio driver; and the body was low-density polyurethane foam rubber material (UL94HF-1).

The first signal source consisted of a waveform generator connected to Class A/B current amplifier. This source was used to drive 2V peak-to-peak sinusoidal voltages in order to determine the transfer function of the isolation mattress 900 in the frequency band of interest. The frequencies used were: 10 Hz, 20 Hz, 30 Hz, 40 Hz, 50 Hz, 60 Hz, 70 Hz, 80 Hz, 90 Hz, 100 Hz and 200 Hz. These individual frequencies were used to de-convolve the system transfer function, but the results are not described herein. The second input source was a signal generator configured in the 30 Hz to 60 Hz range at various output settings (e.g. turns). Due to limited availability of the Balance Engineering generator for part of the testing, the third signal source consisted of ten 100 second recordings of the loaded output of the Balance Engineering generator from 1 turn to 10 turns (in 1 turn increments), sampled at 10 kSps, played back via National Instruments LabVIEW SignalExpress software and a National Instruments PCI-6281 Data Acquisition card connected a custom Class A/B current amplifier.

Figure 13:
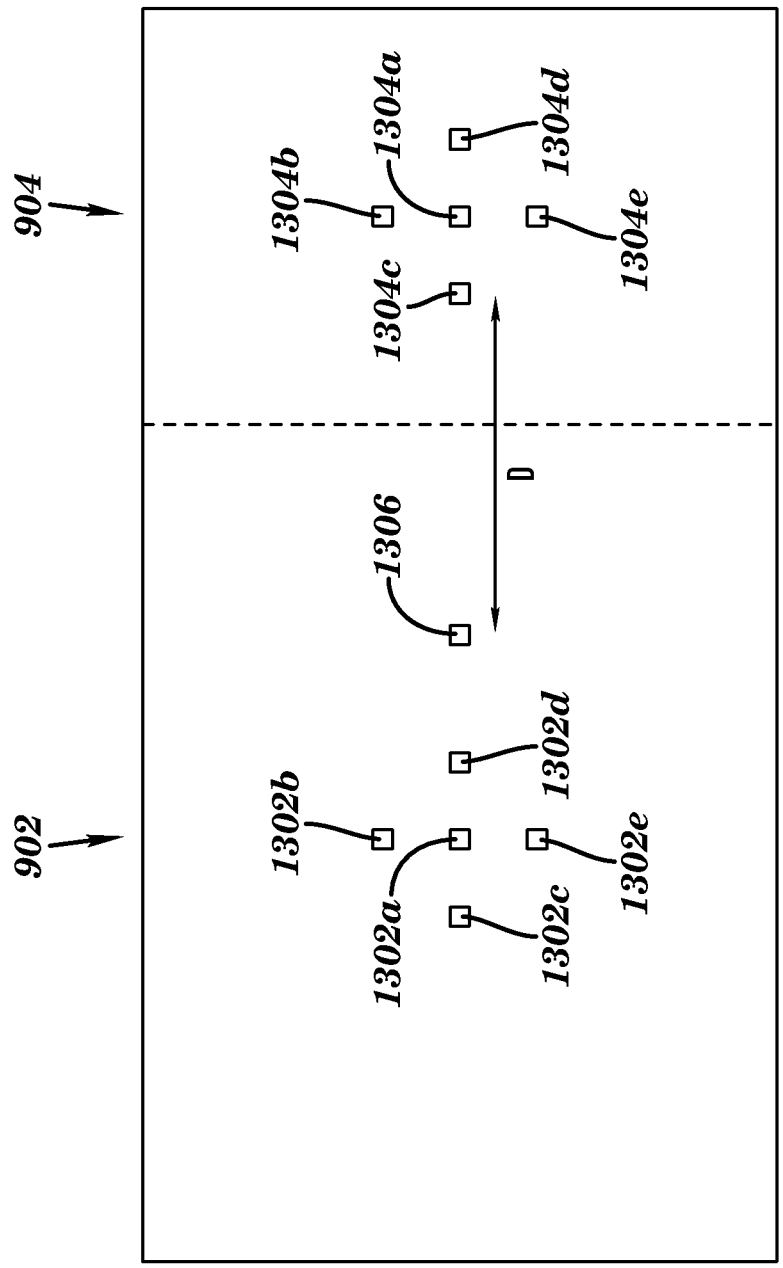
FIG. 13 depicts measurement locations in one embodiment used for the mattress displacement tests.

The isolation mattress was marked with reflective tape for accurate displacement measurements with the MTI-2100. As seen in FIG. 13, tape was placed at centers 1302a, 1304a of the active and passive regions 902, 904, respectively. Tape was also placed at points three inches above, to each side of, and below the centers 1302a, 1302b (1302b-e and 1304b-e, respectively) for a total of ten measurement locations. Measurements were also taken to determine the delivered stimulus and percentage isolation for the head if the infant were placed on the physical center point 1306 of the isolation mattress 900 rather than being placed on the center 1302a of the active region 902. Point 1304c was used to describe displacement at the infant's head because it was 5" away from the mattress center 1306. As with the previous characterization, surface displacement measurements were collected using the MTI-2100 Fotonic Displacement system on an air table in.

All measurements with the MTI-2100 system were taken using a Model 2062R fiber optic probe in its Range 1 measurement configuration. The linear range for the Model 2062R probe the Range 1 configuration was 152 μm with a nominal sensitivity of 0.024 μm. Each recording period was 100 seconds for every test, regardless of stimulus type. The output of the MTI-2100 system was recorded at 10 kSps and stored into a text file using a Tektronix MSO4034B digital oscilloscope. The stimulus drive voltage and drive current were also recorded at this frequency.

The recorded results were processed using MATLAB® in a similar manner to the methods of the previous characterization. Symmetric 3-pole high-pass Butterworth filters (cut-off of 1 Hz) and low-pass Butterworth filters (cut-off of 4 kHz) were applied to the data. The power spectral density was calculated using Welch's method with a spectral frame size of 1 Hz and a resolution sensitivity of 1.1 Hz. The Root-Mean-Squared value for output displacement was computed using a single window because it yielded more accurate results with less computational time than a sliding window of 0.1 seconds.

Figure 11:
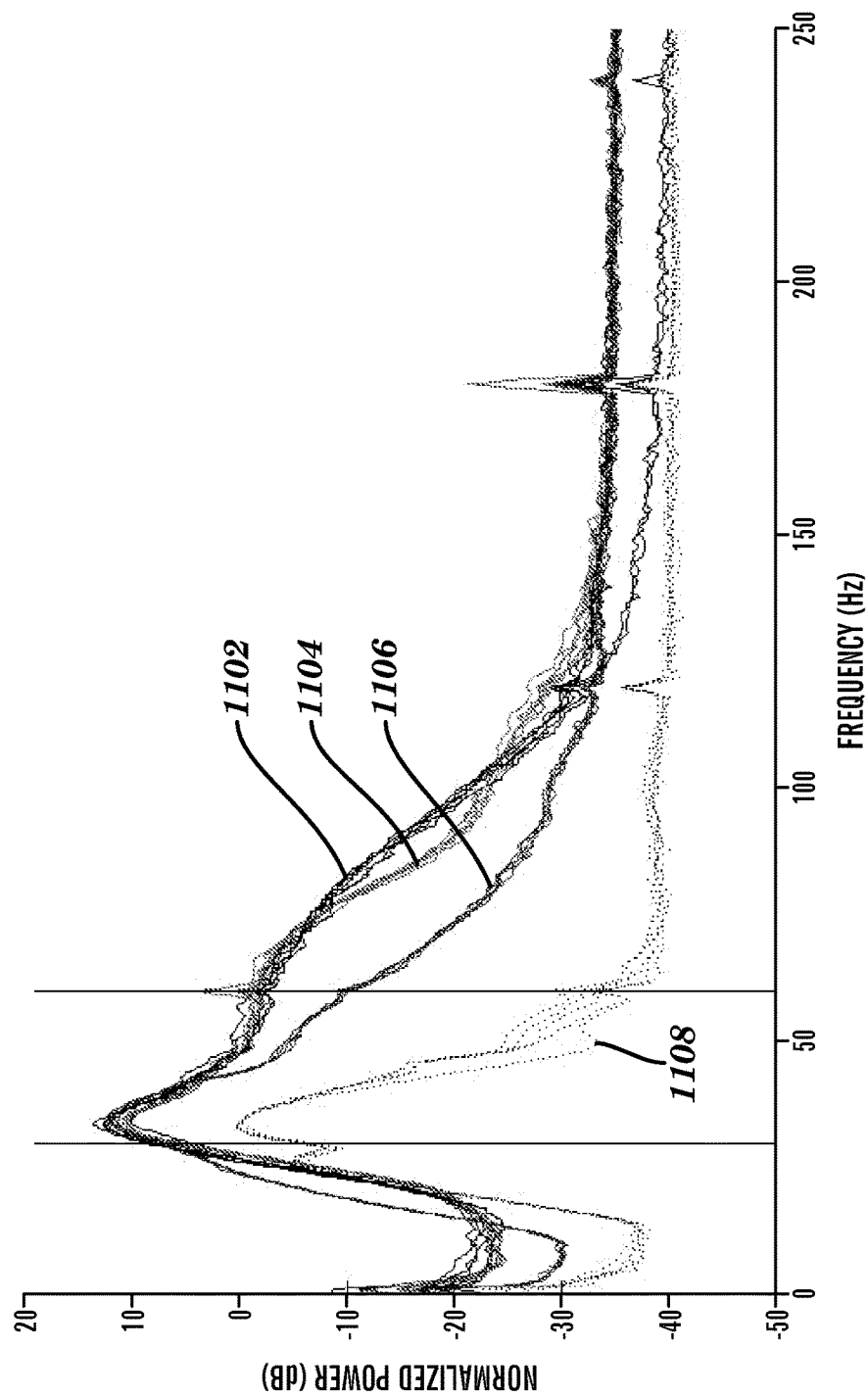
FIG. 11 shows results from the test of the single-bodied mattress compared to the isolation mattress of FIG. 9.

FIG. 11 shows results from the test of the single-bodied mattress compared to the isolation mattress with active and passive regions. The isolation mattress was the same as described in FIG. 9. Line 1102 represents readings from the tested single-bodied mattress at the center of stimulation for 1.5 turns. Line 1104 represents readings from the single-bodied mattress measured at the location of an infant's head for 1.5 turns. Line 1106 represents readings from the isolation mattress measured at the active region center 1302a at 2.75 turns of the signal generator, which was determined to produce the same therapeutic amplitude as the single-bodied mattress at 1.5 turns. Line 1108 represents readings from the isolation mattress measured at the passive region center 1304a at 2.75 turns. The output power spectral density of the isolation mattress closely matched the single-bodied mattress from 4 Hz-43 Hz, but the delivered power drops off from 44 Hz-60 Hz. The difference above 44 Hz may have been caused by the outer vinyl skin of the tested isolation mattress internally adhering to the body of the mattress. A similar attenuation was seen in previous single-bodied mattress characterization when a 1.5 kg mass was placed on the mattress.

Figure 12:
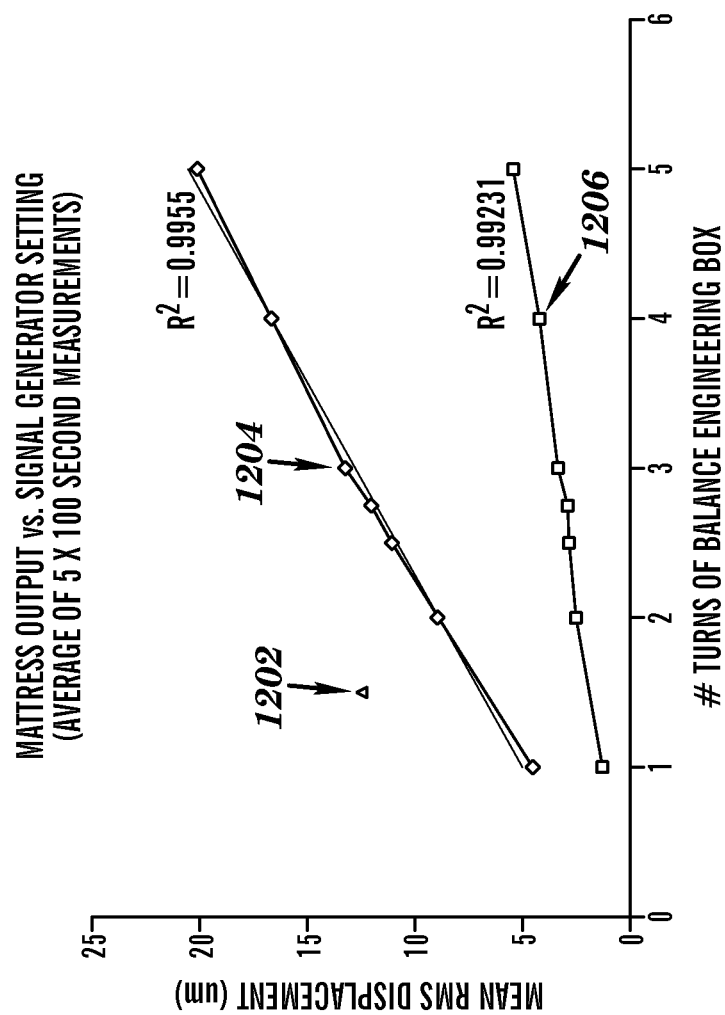
FIG. 12 shows a graph of mattress output for the isolation mattress, comparing the output of the active and passive regions.

Referring now to FIG. 12, a graph of mattress output is shown. Point 1202 is the output of the single-bodied mattress. Line 1204 is the output of isolation mattress at the active region center 1302a. Line 1206 is the output of the isolation mattress at the passive region center 1304a. Table 1 lists the measured values shown in the graph with a calculation of the percent attenuation between the active region center 1302a and the passive region center 1304a.

TABLE 1

RMS Displacement Values and Percent Attenuation for the Isolation Mattress

| Stimulus Generator setting [turns] | Mean Active Region Center RMS Displacement [μm] | Mean Passive Region Center RMS Displacement [μm] | Active Center to Passive Center Attenuation [μm] |
|---|---|---|---|
| 1 | 4.5 | 1.3 | 72.0 |
| 2 | 8.9 | 2.5 | 72.4 |
| 2.5 | 11.0 | 2.8 | 74.7 |
| 2.75 | 12.1 | 2.9 | 76.0 |
| 3 | 13.2 | 3.4 | 74.5 |
| 4 | 16.7 | 4.2 | 74.7 |
| 5 | 20.1 | 5.5 | 72.9 |

As shown in table 1, there was a drastic reduction in displacement between the active center and the passive center. The attenuation between the centers was consistently between 72% and 76% across the tested range. That is, the isolation mattress 900 prevented approximately three quarters of the stimulation of the active region from reaching the passive region.

The secondary positions 1304c, 1306 provide data related to the attenuation of vibration between the approximate the head and body positions of an infant placed on the isolation mattress. Table 2 compares attenuation between an infant's head and body using the above described single-bodied mattress and the isolation mattress 900.

TABLE 2

Comparison of Single-bodied and Isolation Mattresses

| | Stimulus Generator setting [turns] | Mean Mattress Center RMS Displacement [μm] | Mean Head RMS Displacement [μm] | Attenuation [%] |
|---|---|---|---|---|
| Single-bodied | 1.5 | 12.5 | 11.0 | 12.2 |
| Isolation | 2.75 | 8.4 | 2.6 | 69.5 |

Comparing the attenuation of the overall mattress center to the approximate head location for both mattresses resulted in the isolation mattress showing an improvement of 5.7 times over the single-bodied mattress.

The therapeutic level of stimulation of the single-bodied mattress was determined to be 1.5 turns of the amplifier on the noise generator as determined by comparison to previous tests. Therapeutic level of stimulation may be any stimulation that is capable of altering a sleep state or physiological function of sufficient amplitude to cause harm or pain. This includes subthreshold, subarousal, and/or suprathreshold stimulation. The isolation mattress was tested to determine the turns needed to achieve an equivalent level of output stimulation. It was determined that 2.75 turns was the appropriate therapeutic setting for the isolation mattress. At this setting, the mean root-mean-squared displacement of the center 1302a of the active region 902 is comparable to the therapeutic displacement of the geometric center of the single-bodied mattress.

Sensors for direct monitoring and/or control of mattress surface displacement may be incorporated with the isolation mattress 900. These sensors can include, for example, embedded accelerometers or other vibratory sensors (e.g. pressure sensors, load cells, optical sensors). Such sensors can be used, for example, in modifying the drive signal for the active region in response to weight, loading, or the location of the infant on the mattress. Such sensors can be used, for example, in alerting caregivers to malfunctions or even active cancellation of stimulation in the passive region.

Focal Stimulation

In another embodiment, focal stimulation may be used to apply stochastic resonance stimulation to a subject. Systemic vibration may be potentially inappropriate for patients who are at risk of intra-ventricular hemorrhage. Instead, focal stimulation can be used to both discover and target the correct mechanoreceptors to therapeutically address different modes of respiratory instability. Additionally, focal stimulation can deliver only the essential stimulation when required. Focal stimulators may be used to apply mechanical stochastic resonance stimulation to improve the respiratory function of infants at risk of apnea or other respiratory instabilities. The stimulation may be applied in both open- and closed-loop fashions.

Figure 14:
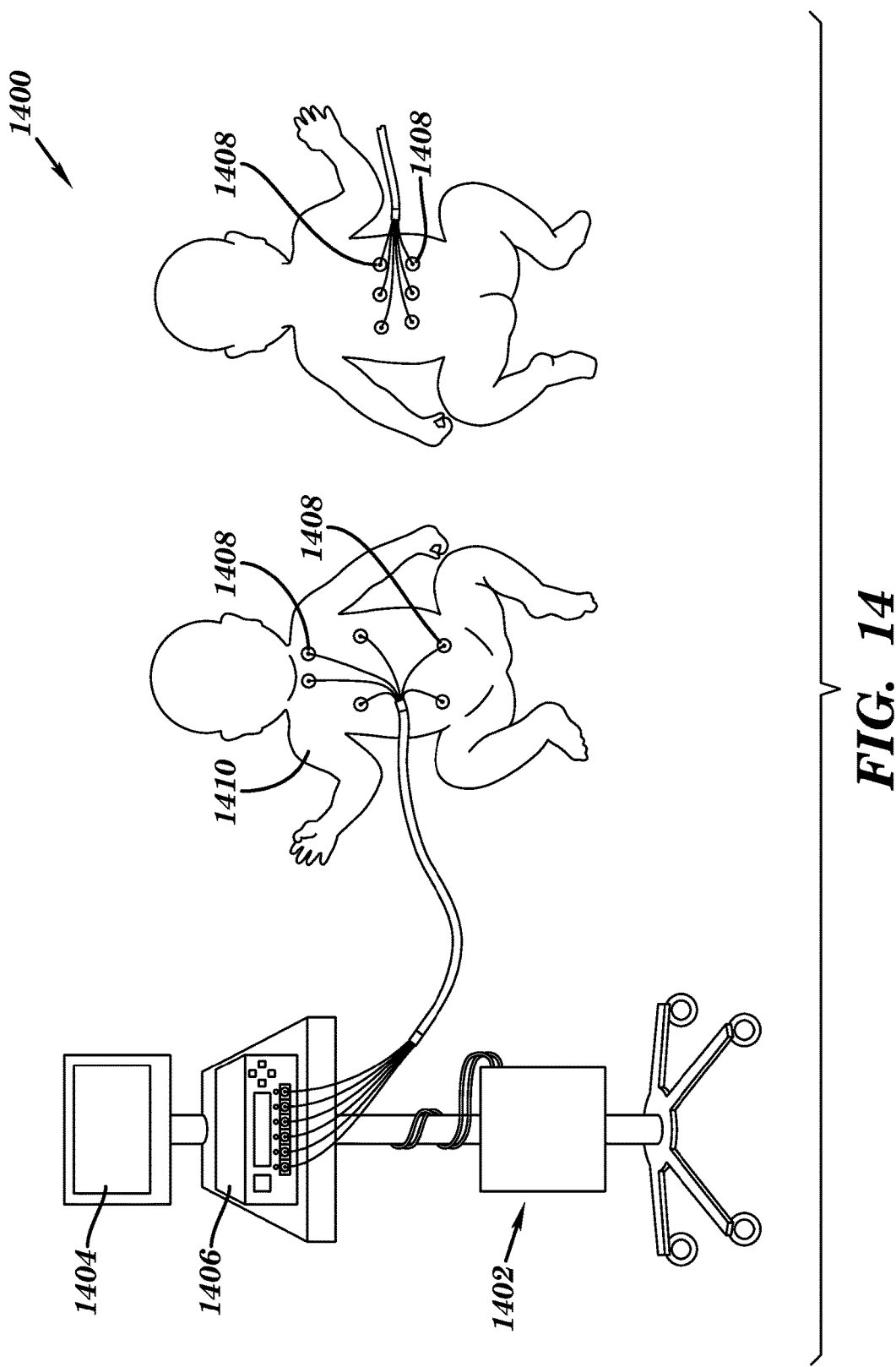
FIG. 14 shows a system for focal stimulation according to one embodiment.

Referring now to FIG. 14, a focal system 1400 is shown according to one embodiment. The system 1400 includes a processor 1402, a user interface 1404, a signal generator 1406 and a plurality of focal stimulators 1408. The focal stimulators 1408 are applied to a body of a subject 1410 to stimulate to the subject. The system may additionally include a communications bus, data logging mechanism, and/or connections for input sensors. The communications bus provides an interface to attach external master controllers such as a laptop to the system 1400. The data logging mechanism may be used to locally store and/or report data. Input sensors such as temperature sensors, accelerometers, strain gages, pulse-oximeters, plethysmographs and other physiologic monitoring sensor systems may interface with the system to provide physiological information related to subject. This physiological information may be monitored and used by the system to initiate or alter stimulation.

The focal stimulators 1408 may be comprised of one type or a combination of types of actuators including electromagnetic, electromechanical, solid state actuators (e.g., Nitinol, piezoelectric), hydraulic, pneumatic, ferrofluid, electroactive polymer, etc. In the illustrated embodiment, the plurality of focal stimulators 1408 is designed to be placed in direct contact with the subject's skin. Thus, in this embodiment, it is desirable for the focal stimulators 1408 to be formed from biocompatible and/or hypoallergenic materials. For safety, the focal stimulators may also include double-electrical insulation so that the subject is protected from electrical discharge or electromagnetic interference.

The signal generator 1406 drives the focal stimulators 1408 and may drive them individually, in groups, or even as one unit. The signal generator 1406 may be, for example, a stochastic resonance noise generator and may include adjustable drive capabilities to ensure the delivery of adequate stimulation. The needed signal may be affected by conditions such as the stimulators being placed in an intervening brace or other mediating material. The focal stimulators 1408 may be applied to the subject using a number of materials such as braces, fitted garments, elastic bands, FDA-approved adhesives, etc.

The system 1400 may be used to control and optimize focal stimulation in response to an infant's real-time physiological status. For example, the system may monitor the infant's respiratory pattern and initiate stimulation to prevent or inhibit the occurrence of an impending apneic event. Additionally, the system 1400 may be used in developing algorithms to control and optimize focal stimulation. The use of physiological input sensors allows the device both to self-calibrate and deliver the correct stimulation independently of the attachment method and to dynamically adapt that stimulation during use.

Figure 15A:
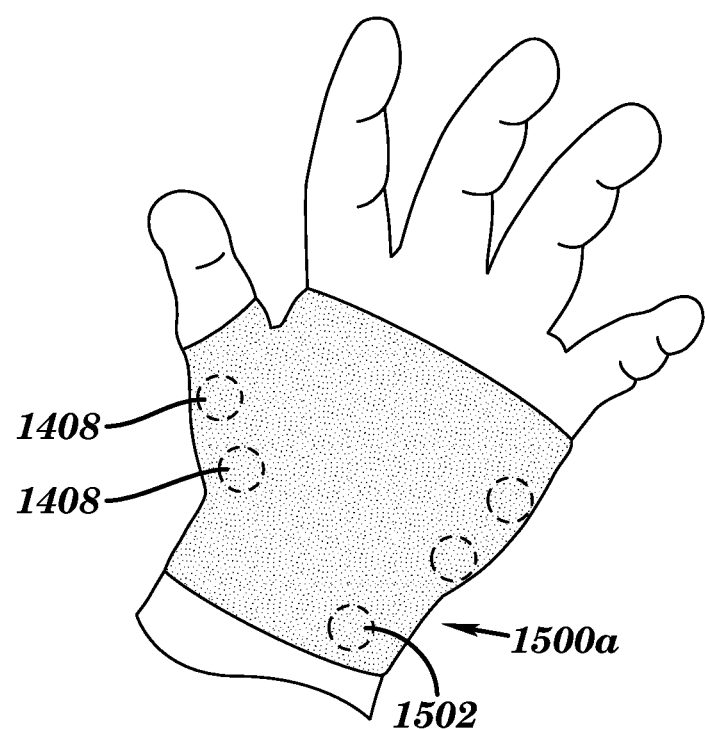
FIG. 15A shows a support structure or garment according to one embodiment.
Figure 15B:
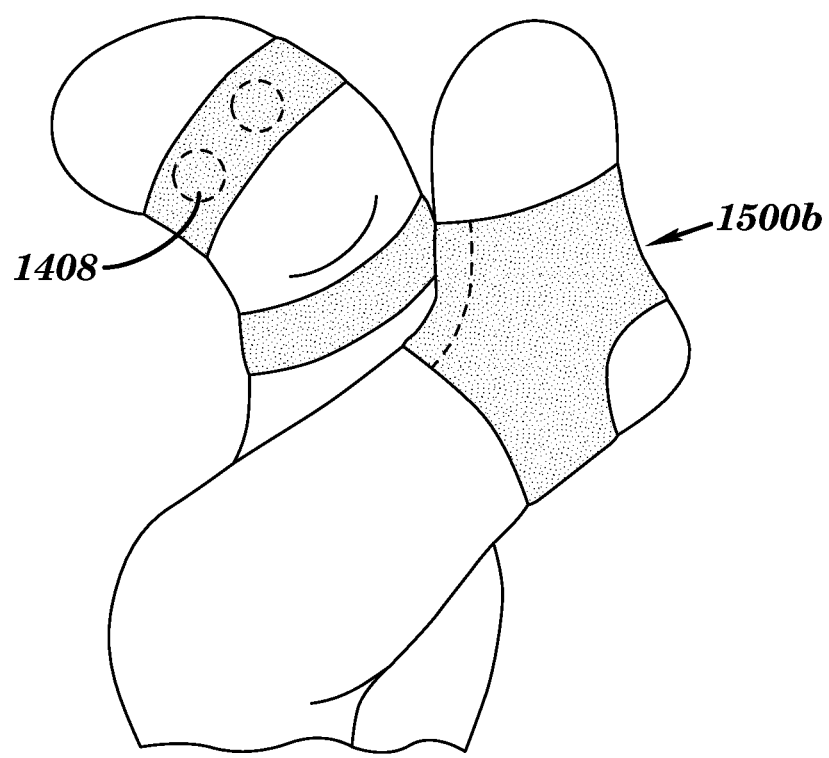
FIG. 15B shows a support structure or garment according to another embodiment.

Referring now to FIGS. 15A and 15B, non-limiting examples of support garment structures for embedded focal stimulators are shown. Support garment structures may be made of a variety of materials including flexible materials such as neoprene, latex, rubber, silicone, cloth, wool, vinyl, polyvinyl chloride, nitrile, neoprene, knit textiles, composites, or leather. FIG. 15A shows a hand support structure 1500*a* that fits on the hand of an infant. The hand support structure 1500*a* includes a plurality of focal stimulators 1408 configured to apply stimulation to an isolated body part of the infant. In the illustrated embodiment, the body part is the infant's hand. Additionally, the hand support structure 1500*a* includes an input sensor such as, temperature sensors, blood pressure sensors 1502, accelerometers, strain gauges, pulse-oximeters, plethysmographs, and other physiological monitoring sensor systems that will assist in enabling the embedded focal stimulators 1408 during an apneic episode. FIG. 15B shows a foot support structure 1500*b* that fits on the foot of an infant and includes embedded focal stimulators 1408.

It is contemplated that the system may be condensed to a single embedded controller. The embedded controller includes algorithms developed to optimize the stimulation level and stimulation timing, and includes the integration of multiple types of sensors. The embedded controller may autonomously control the application of stochastic resonance stimulation based on either input sensors or a physician's programmed therapeutic regimen. These input sensors monitor at least one physiological condition. The placement and method of attachment of the focal stimulators 1408 also factor into the algorithm for the application of stimulation. Such a system may be condensed, simplified, and battery powered so that it may be designed for safe and efficacious use in home environments. Additionally, portions of the system such as sensors may communicate wirelessly with other portions of the system to decrease wires and increase safety.

Array Stimulation

In yet another embodiment, array stimulation may be used to apply stochastic resonance stimulation to a subject. Array stimulation can be used to deliver targeted stimulation while covering an area for potential stimulation. Additionally, array stimulation can deliver synchronized stimulation patterns over the array. Array stimulators may be used, for example, to apply stochastic resonance stimulation to improve the respiratory function of infants at risk of apnea or other respiratory instabilities. The stimulation may be applied in various ways such as single-actuator stimulation, multiple-actuator stimulation, or even coordinated stimulation such as stroking.

Figure 16A:
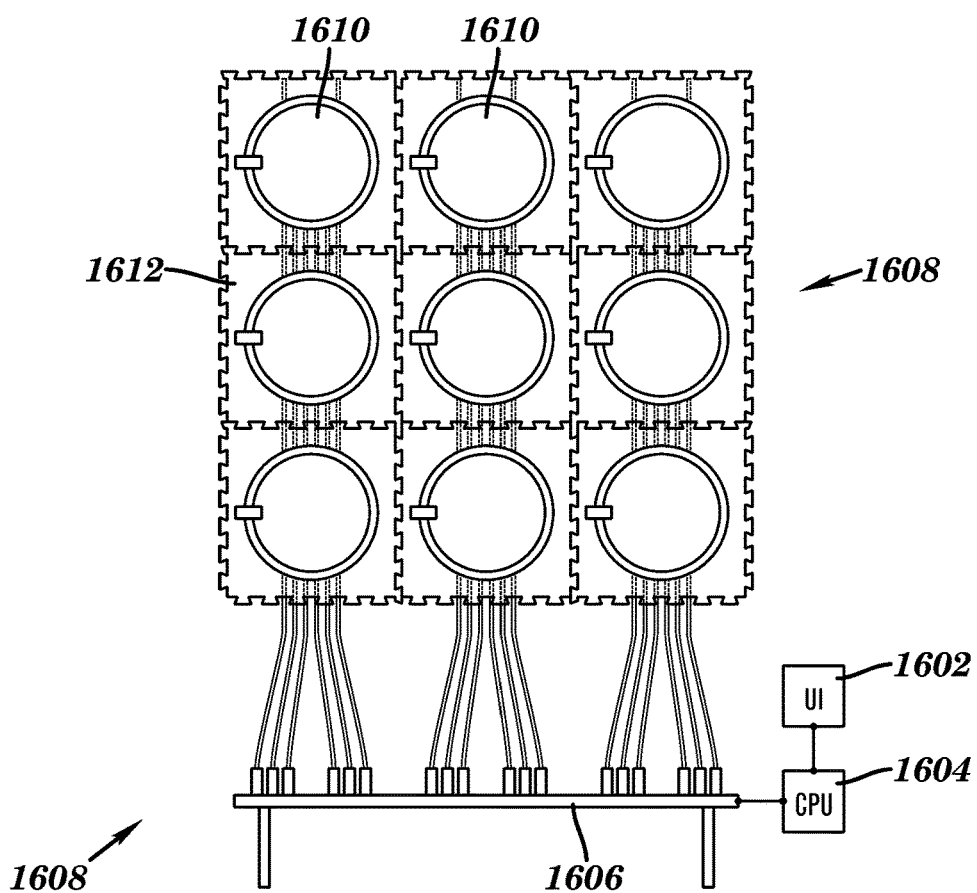
FIG. 16A depicts stimulation array according to one embodiment.
Figure 16B:
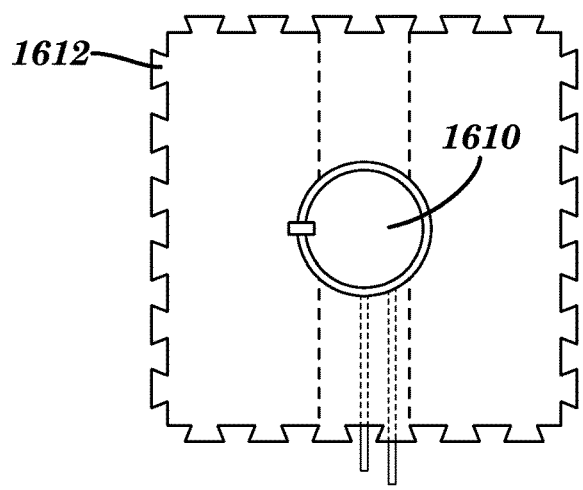
FIG. 16B depicts single piece of the stimulation array.

FIG. 16A depicts a stimulation array system 1600 according to one embodiment. The stimulation array system 1600 includes a user interface 1602, a processor 1604, a controller 1606, and a stimulation array 1608. The stimulation array includes stimulators 1610 to stimulate a subject. Other components may include a communications bus, data logging mechanism, and/or connections for input sensors.

The user interface 1602 allows the user to interact with the stimulation array system 1600 and is operatively connected to the processor 1604. The processor 1604 is operatively connected to the controller 1606. The controller 1606 is operatively connected to the stimulation array 1608 and drives the stimulators 1610. In this embodiment the stimulators 1610 are driven independently. It is contemplated that the stimulators 1610 may also be driven in groups.

In this embodiment stimulation array 1608 includes interlocking pieces 1612. Each interlocking piece 1612 includes a single stimulator 1610. By way of non-limiting example the stimulators may be electromagnetic, electromechanical, solid state actuators (e.g., Nitinol, piezoelectric), hydraulic, pneumatic, ferrofluid, electroactive polymer, etc. it is contemplated that more than one stimulator 1610 may be included on an interlocking piece 1612. It is additionally contemplated that the stimulation array 1608 may be a single mat.

The array system 1600 may be used to control and optimize focal stimulation in response to an infant's real-time physiological status. For example, the system may monitor the infant's respiratory pattern and initiate stimulation to prevent or inhibit the occurrence of an impending apneic event. The use of physiological input sensors allows the device both to self-calibrate and deliver the correct stimulation independently of the attachment method and to dynamically adapt that stimulation during use.

Additionally, the array system 1600 may include sensors to detect the location of a child on the stimulation array 1608. Detecting the location of the child allows the array system 1600 to target stimulation. This targeted stimulation can be used to deliver stimulation only to portions of the stimulation array 1608 occupied by the child, simulate a stroking motion, or simulate a wave motion. Additionally, detecting the location may also be used to determine orientation of a child. Determining orientation would allow for targeted stimulation of the child's body without stimulating the child's head regardless of the child's location. The sensors to determine location may be included with the stimulation array 1608 or may be independent of the stimulation array 1608.

In accordance with the above embodiments, the vibrotactile stimulation can be turned on and turned off for a predefined periods of time. Alternatively the vibrotactile stimulation can remain on until a change in one or more aspects of the breathing pattern are detected. Further, the nature of the stimulation can change over time such that the amplitude, frequency characteristics, and/or period of vibration can change over time.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents, and alternatives falling within the spirit and scope of the invention as defined by the appended claims.

What is claimed is:

1. A method for inhibiting a future apneic event comprising steps of:
   monitoring physiological data of an infant with one or more sensors, the one or more sensors comprising a respiration sensor, the physiological data including measurements of an interbreath interval of the infant;
   receiving the physiological data from the one or more sensors into a sensor and data acquisition system;
   producing the physiological data from the sensor and data acquisition system to input to a signal processor;
   analyzing, via an algorithm of the signal processor, the input physiological data to detect an impending apneic event;
   predicting the impending apneic event using a point-process model, the predicting being based on a variance, $\sigma^2$, of the measurements and a predetermined threshold value of the interbreath interval, the predetermined threshold value indicating a predetermined event of the impending apneic event;
   comparing via a compare module the variance to the predetermined threshold value;
   determining that the variance is greater than the predetermined threshold value; and
   based on the determining, automatically applying a subarousal vibrational stimulation to the infant via a physical stimulator to inhibit occurrence of the impending apneic event by reducing or eliminating the variance, the physical stimulator interacting with one or more body parts of the infant, the subarousal vibrational stimulation including stochastic resonance stimulation.

2. The method of claim 1 wherein the subarousal vibrational stimulation is a vibrational stimulus applied through a mattress.

3. The method of claim 1 wherein the subarousal vibrational stimulation is applied to focused areas on the body of the infant.

4. The method of claim 1 wherein the physical stimulator includes at least one actuator.

5. The method of claim 1 wherein the receiving step and the analyzing step occur in real time.

6. The method of claim 1, further comprising sending a notification to an individual regarding the impending apneic event.

7. The method of claim 1, wherein the physiological data includes other respiratory data.

8. The method of claim 1, wherein the physiological data includes cardiological data.

9. The method of claim 1, wherein the physiological data includes body motion data.

* * * * *